(12) United States Patent
Smith et al.

(10) Patent No.: US 8,333,807 B2
(45) Date of Patent: Dec. 18, 2012

(54) METHOD AND APPARATUS FOR TRIALING AND IMPLANTING A MODULAR FEMORAL HIP

(75) Inventors: Aaron P. Smith, Warsaw, IN (US); Tyler D. Witt, Fond du Lac, WI (US)

(73) Assignee: Biomet Manufacturing Corp., Warsaw, IN (US)

( * ) Notice: Subject to any disclaimer, the term of this patent is extended or adjusted under 35 U.S.C. 154(b) by 417 days.

(21) Appl. No.: 12/718,031

(22) Filed: Mar. 5, 2010

(65) Prior Publication Data
US 2011/0218640 A1 Sep. 8, 2011

(51) Int. Cl.
*A61F 2/32* (2006.01)
(52) U.S. Cl. .................. 623/22.42; 623/20.35
(58) Field of Classification Search .......... 606/102; 623/23.44
See application file for complete search history.

(56) References Cited

U.S. PATENT DOCUMENTS

| | | |
|---|---|---|
| 2,231,864 A | 2/1941 | Abel |
| 3,815,599 A | 6/1974 | Deyerle |
| 4,306,550 A | 12/1981 | Forte |
| 4,549,319 A | 10/1985 | Meyer |
| 4,552,136 A | 11/1985 | Kenna |
| 4,601,289 A | 7/1986 | Chiarizzio et al. |
| 4,718,915 A | 1/1988 | Epinette |
| 4,728,333 A | 3/1988 | Masse et al. |
| 4,790,852 A | 12/1988 | Noiles |
| 4,842,606 A | 6/1989 | Kranz et al. |
| 4,883,492 A | 11/1989 | Frey et al. |
| 4,904,269 A | 2/1990 | Elloy et al. |
| 4,959,066 A | 9/1990 | Dunn et al. |
| 5,041,118 A | 8/1991 | Wasilewski |
| 5,047,035 A | 9/1991 | Mikhail et al. |
| 5,061,271 A | 10/1991 | Van Zile |
| 5,089,004 A | 2/1992 | Averill et al. |
| 5,092,900 A | 3/1992 | Marchetti et al. |
| 5,122,146 A | 6/1992 | Chapman et al. |
| 5,201,769 A | 4/1993 | Schutzer |
| 5,211,666 A | 5/1993 | Fetto |
| 5,409,492 A | 4/1995 | Jones et al. |

(Continued)

FOREIGN PATENT DOCUMENTS
DE 29516473 U1 12/1995
(Continued)

OTHER PUBLICATIONS

DePuy, a Johnson & Johnson company, "REEF: Distally Interlocked Modular Femoral Reconstruction Prosthesis", 2004, 7 sheets.

(Continued)

*Primary Examiner* — David H Willse
*Assistant Examiner* — Javier Blanco
(74) *Attorney, Agent, or Firm* — Harness, Dickey

(57) ABSTRACT

A modular femoral hip implant trialing system. The system generally includes a proximal body, a fastener, and a fastener retention member. The proximal body includes a proximal bore, a tapered distal bore, and a passageway connecting the proximal bore to the distal bore. The proximal bore, the distal bore, and the passageway are aligned along a first axis. The fastener includes a head in the proximal bore and a stem in the distal bore, the fastener is aligned along the first axis. The fastener retention member is positioned in the proximal bore and is operable to retain at least a portion of the fastener within the proximal bore.

18 Claims, 18 Drawing Sheets

U.S. PATENT DOCUMENTS

| | | | |
|---|---|---|---|
| 5,468,243 | A | 11/1995 | Halpern |
| 5,489,284 | A | 2/1996 | James et al. |
| 5,562,666 | A | 10/1996 | Brumfield |
| 5,571,111 | A | 11/1996 | Aboczky |
| 5,578,037 | A | 11/1996 | Sanders et al. |
| 5,601,564 | A | 2/1997 | Gustilo et al. |
| 5,607,431 | A | 3/1997 | Dudasik et al. |
| 5,632,747 | A | 5/1997 | Scarborough et al. |
| 5,645,549 | A | 7/1997 | Boyd et al. |
| 5,649,930 | A | 7/1997 | Kertzner |
| 5,665,090 | A | 9/1997 | Rockwood et al. |
| 5,690,636 | A | 11/1997 | Wildgoose et al. |
| 5,699,915 | A | 12/1997 | Berger et al. |
| 5,704,940 | A | 1/1998 | Garosi |
| 5,766,261 | A | 6/1998 | Neal et al. |
| 5,788,701 | A | 8/1998 | McCue |
| 5,849,015 | A | 12/1998 | Haywood et al. |
| 5,860,969 | A | 1/1999 | White et al. |
| 5,860,982 | A | 1/1999 | Ro et al. |
| 5,908,423 | A | 6/1999 | Kashuba et al. |
| 5,913,860 | A | 6/1999 | Scholl |
| 5,976,145 | A | 11/1999 | Kennefick, III |
| 5,989,261 | A | 11/1999 | Walker et al. |
| 6,022,357 | A | 2/2000 | Reu et al. |
| 6,027,505 | A | 2/2000 | Peter et al. |
| 6,033,405 | A | 3/2000 | Winslow et al. |
| 6,110,179 | A | 8/2000 | Flivik et al. |
| 6,110,211 | A | 8/2000 | Weiss |
| 6,117,138 | A | 9/2000 | Burrows et al. |
| 6,117,173 | A | 9/2000 | Taddia et al. |
| 6,126,694 | A | 10/2000 | Gray, Jr. |
| 6,136,035 | A | 10/2000 | Lob et al. |
| 6,139,551 | A | 10/2000 | Michelson et al. |
| 6,143,030 | A | 11/2000 | Schroder |
| 6,152,963 | A | 11/2000 | Noiles et al. |
| RE37,005 | E | 12/2000 | Michelson et al. |
| 6,159,216 | A | 12/2000 | Burkinshaw et al. |
| 6,224,605 | B1 | 5/2001 | Anderson et al. |
| 6,224,609 | B1 | 5/2001 | Ressemann et al. |
| 6,238,435 | B1 | 5/2001 | Meulink et al. |
| 6,245,111 | B1 | 6/2001 | Shaffner |
| 6,267,785 | B1 | 7/2001 | Masini |
| 6,302,890 | B1 | 10/2001 | Leone, Jr. |
| 6,306,174 | B1 * | 10/2001 | Gie et al. ............ 623/22.42 |
| 6,330,845 | B1 | 12/2001 | Meulink |
| 6,338,734 | B1 | 1/2002 | Burke et al. |
| 6,344,060 | B1 | 2/2002 | Schmotzer et al. |
| 6,361,565 | B1 | 3/2002 | Bonutti |
| 6,371,991 | B1 | 4/2002 | Manasas et al. |
| 6,395,004 | B1 | 5/2002 | Dye et al. |
| 6,468,281 | B1 | 10/2002 | Badorf et al. |
| 6,517,581 | B2 | 2/2003 | Blamey |
| 6,626,913 | B1 | 9/2003 | McKinnon et al. |
| 6,871,549 | B2 | 3/2005 | Serra et al. |
| 6,875,239 | B2 * | 4/2005 | Gerbec et al. ............ 623/23.15 |
| 6,883,217 | B2 | 4/2005 | Barrette et al. |
| 6,913,623 | B1 | 7/2005 | Zhu |
| 6,932,819 | B2 | 8/2005 | Wahl et al. |
| 7,074,224 | B2 * | 7/2006 | Daniels et al. ............ 606/80 |
| 7,179,259 | B1 | 2/2007 | Gibbs |
| 7,210,881 | B2 | 5/2007 | Greenberg |
| 7,247,171 | B2 | 7/2007 | Sotereanos |
| 7,255,716 | B2 | 8/2007 | Pubols et al. |
| 7,291,176 | B2 | 11/2007 | Serra et al. |
| 7,297,166 | B2 | 11/2007 | Dwyer et al. |
| 7,341,589 | B2 | 3/2008 | Weaver et al. |
| 7,425,214 | B1 * | 9/2008 | McCarthy et al. ............ 606/89 |
| 7,491,242 | B2 | 2/2009 | Pichon et al. |
| 7,582,092 | B2 | 9/2009 | Jones et al. |
| 7,585,301 | B2 * | 9/2009 | Santarella et al. ............ 606/99 |
| 7,585,329 | B2 * | 9/2009 | McCleary et al. ......... 623/23.15 |
| 7,832,405 | B1 | 11/2010 | Schlueter et al. |
| 7,857,858 | B2 * | 12/2010 | Justin et al. ............ 623/20.34 |
| 2003/0233100 | A1 | 12/2003 | Santarella et al. |
| 2004/0107001 | A1 | 6/2004 | Cheal et al. |
| 2004/0122439 | A1 | 6/2004 | Dwyer et al. |
| 2004/0236341 | A1 | 11/2004 | Petersen |
| 2005/0203539 | A1 | 9/2005 | Grimm et al. |
| 2006/0004459 | A1 * | 1/2006 | Hazebrouck et al. ...... 623/18.12 |
| 2007/0093844 | A1 | 4/2007 | Dye |
| 2007/0123908 | A1 * | 5/2007 | Jones et al. ............ 606/102 |
| 2007/0129809 | A1 | 6/2007 | Meridew et al. |
| 2008/0125867 | A1 * | 5/2008 | McCleary et al. ........... 623/22.4 |
| 2008/0154276 | A1 | 6/2008 | Pubols et al. |
| 2008/0161811 | A1 | 7/2008 | Daniels et al. |
| 2008/0208203 | A1 * | 8/2008 | Moindreau et al. ........ 606/102 |
| 2008/0234685 | A1 | 9/2008 | Gjerde |
| 2008/0269765 | A1 | 10/2008 | Banerjee et al. |
| 2008/0294168 | A1 | 11/2008 | Wieland |
| 2009/0099566 | A1 | 4/2009 | Maness et al. |
| 2009/0112218 | A1 | 4/2009 | McCleary et al. |
| 2009/0265014 | A1 | 10/2009 | May et al. |
| 2011/0046745 | A1 * | 2/2011 | Daniels et al. ............ 623/22.42 |

FOREIGN PATENT DOCUMENTS

| | | |
|---|---|---|
| EP | 0453695 A1 | 10/1991 |
| FR | 2676172 A1 | 11/1992 |
| GB | 2299758 A | 10/1996 |
| WO | WO-94/21199 A1 | 9/1994 |
| WO | WO-2007/106752 A2 | 9/2007 |

OTHER PUBLICATIONS

Zimmer, Inc., "ZMR Hip System", 2004, 19sheets.

* cited by examiner

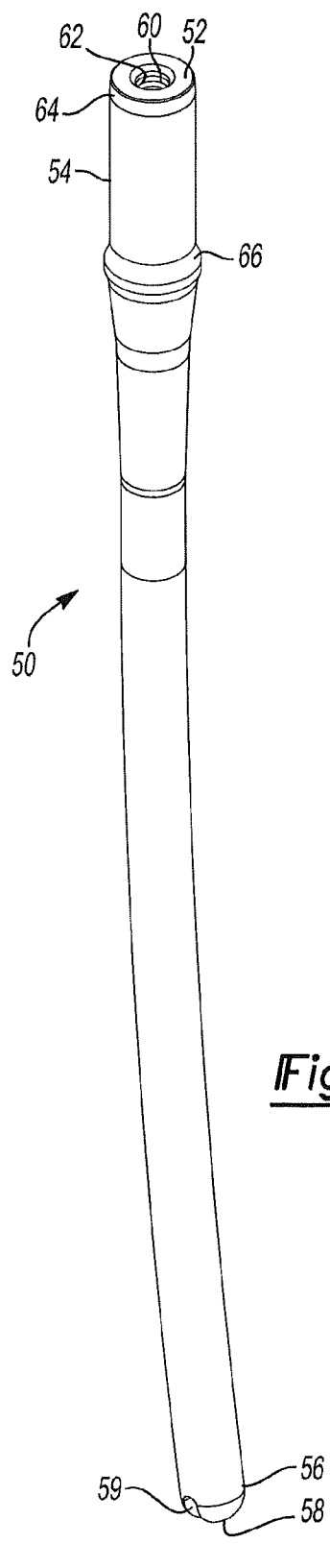
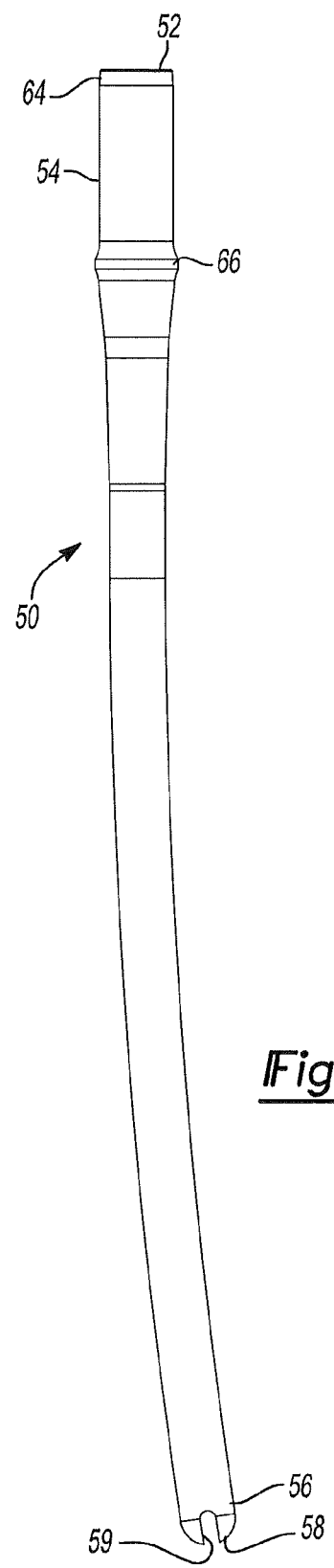
Fig-5
Fig-6

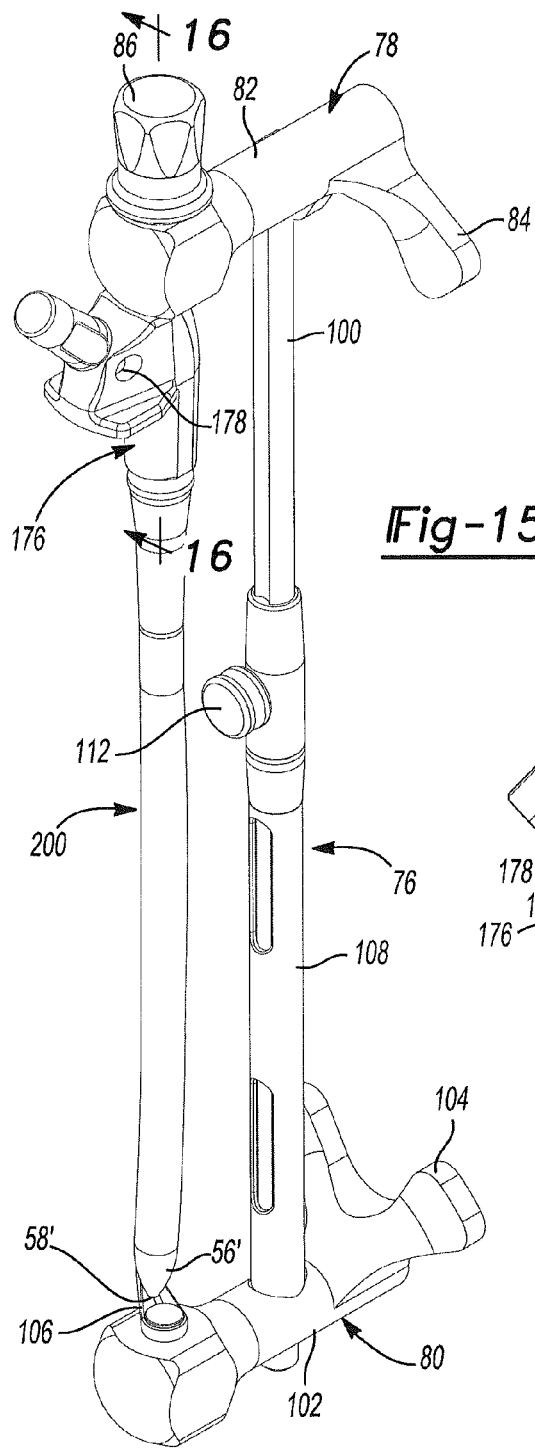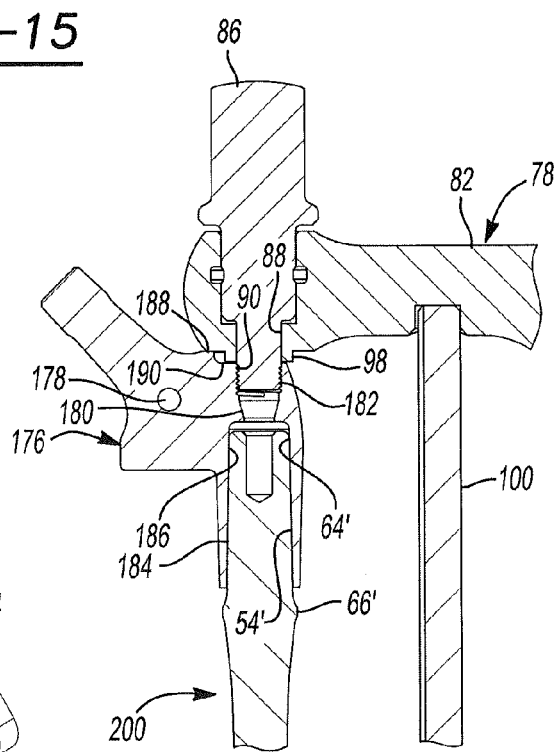
Fig-15
Fig-16

METHOD AND APPARATUS FOR TRIALING AND IMPLANTING A MODULAR FEMORAL HIP

CROSS-REFERENCE TO RELATED APPLICATIONS

This application is related to U.S. patent application Ser. No. 12/718,018 filed Mar. 5, 2010, entitled "METHOD AND APPARATUS FOR IMPLANTING A MODULAR FEMORAL HIP;" U.S. patent application Ser. No. 12/718,230 filed Mar. 5, 2010, entitled "MODULAR LATERAL HIP AUGMENTS;" U.S. patent application Ser. No. 12/718,023 filed Mar. 5, 2010, entitled "GUIDE ASSEMBLY FOR LATERAL IMPLANTS AND ASSOCIATED METHODS;" U.S. patent application Ser. No. 12/718,026 filed Mar. 5, 2010, entitled "REVISION BROACH WITH SMOOTH LATERAL SIDE;" and U.S. patent application Ser. No. 12/718,027 filed Mar. 5, 2010, entitled "ASSEMBLY TOOL FOR MODULAR IMPLANTS AND ASSOCIATED METHOD;" each filed concurrently herewith. The disclosures of each of the above applications are incorporated herein by reference.

FIELD

The present disclosure relates to methods and apparatus for trialing and implanting a modular implant, such as a femoral hip.

BACKGROUND

This section provides background information related to the present disclosure, which is not necessarily prior art.

Modular femoral implants often include a proximal body portion and a distal stem portion. The distal stem is curved or bowed to approximate the natural bow of a femur. During trialing, a trial distal stem is inserted in a reamed femoral canal to determine the proper orientation of the trial distal stem relative to the proximal body portion. This orientation is recreated in the implant when the distal and proximal portions are attached.

SUMMARY

This section provides a general summary of the disclosure, and is not a comprehensive disclosure of its full scope or all of its features.

The present teachings provide for a modular femoral hip implant trialing system. The system generally includes a proximal body, a fastener, and a fastener retention member. The proximal body includes a proximal bore, a tapered distal bore, and a passageway connecting the proximal bore to the distal bore. The proximal bore, the distal bore, and the passageway are aligned along a first axis. The fastener includes a head in the proximal bore and a stem in the distal bore, the fastener is aligned along the first axis. The fastener retention member is positioned in the proximal bore and is operable to retain at least a portion of the fastener within the proximal bore.

The present teachings further provide for a modular femoral hip implant trialing system. The system generally includes a proximal body, a fastener, a washer, and a fastener retention member. The proximal body defines a proximal bore, a distal bore, and a passageway connecting the proximal bore to the distal bore. The proximal bore is axially aligned with the distal bore along a first axis. The fastener has a head in the proximal bore and a stem in the distal bore. The washer is between the head and a base of the proximal bore. The fastener retention member is in the proximal bore. The retention member and the washer are on opposite sides of the head. The retention member includes an aperture having a diameter smaller than a diameter of the head to retain the fastener within the proximal bore.

The present teachings also provide for a modular femoral hip implant trialing system. The system generally includes a proximal body, a fastener, a rotational locking device, and a fastener retention member. The proximal body defines a proximal bore, a distal bore, and a passageway connecting the proximal bore to the distal bore. The proximal bore is axially aligned with the distal bore along a first axis. The fastener has a head in the proximal bore and a stem in the distal bore. The rotational locking device is mounted in the distal bore and surrounds the stem. The rotational locking device includes an inner diameter that is larger than an outer diameter of the stem. The fastener retention member is in the proximal bore between the passageway and the head and is operable to retain the fastener within the proximal bore.

The present teachings further provide for a modular femoral hip implant trialing system. The system generally includes a proximal alignment jig portion, a distal alignment jig portion, and a support rod. The proximal alignment jig portion includes a support device that is operable to support a proximal body having a distal stem mounted thereto. The distal alignment jig portion includes an alignment guide that is operable for use in identifying a first orientation of the distal stem relative to the proximal body. The alignment guide is axially aligned with the support device. The support rod connects the proximal alignment jig portion to the distal alignment jig portion.

The present teachings also provide a modular femoral hip implant trialing method that includes the following: mounting a trial distal stem to a proximal trialing device by mating a first tapered surface of the trial distal stem with a second tapered surface of the proximal trialing device and by mating a fastening device of the proximal trialing device with a receptacle of the trial distal stem so as to permit rotation of the proximal trialing device with respect to the trial distal stem; inserting the trial distal stem in an intramedullary canal of a femur for trialing to determine the appropriate orientation of the proximal trialing device relative to the trial distal stem; locking the proximal trialing device to the trial distal stem by rotating the fastening device to drive the fastening device within the receptacle and to further mate the first tapered surface with the second tapered surface to prevent rotation therebetween after trialing; mounting the proximal trialing device to a proximal portion of an alignment jig; identifying and recording a position of the trial distal stem relative to the proximal trialing device with an alignment guide at a distal portion of the alignment jig; removing the proximal trialing device with the trial distal stem mounted thereto from engagement with the alignment jig; mounting a proximal body implant to the proximal portion of the alignment jig; mounting a distal stem implant to the proximal body implant such that a tip of the distal stem implant approximates the position of the trial distal stem recorded relative to the alignment guide to provide the distal stem implant and the proximal body implant with a relative orientation that is similar to the orientation of the proximal trialing device relative to the trial distal stem during trialing; and implanting the distal stem implant with the proximal body implant mounted thereto in the intramedullary canal of the femur.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is perspective view of a trial distal stem according to the present teachings;

FIG. 6 is a side view of the trial distal stem of FIG. 5;

FIG. 15 is a perspective view of a distal stem implant mounted to a proximal body implant mounted in the alignment jig assembly to set the orientation of the distal stem implant relative to the proximal body implant;

FIG. 16 is a cross-sectional view taken along line 16-16 of FIG. 15;

Corresponding reference numerals indicate corresponding parts throughout the several views of the drawings.

DETAILED DESCRIPTION

Figure 1:
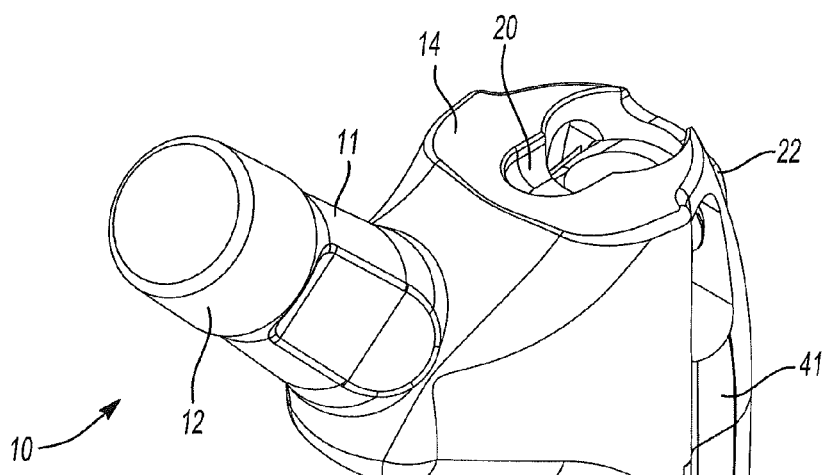
FIG. 1 is a perspective view of a trial proximal component according to the present teachings.
Figure 2:
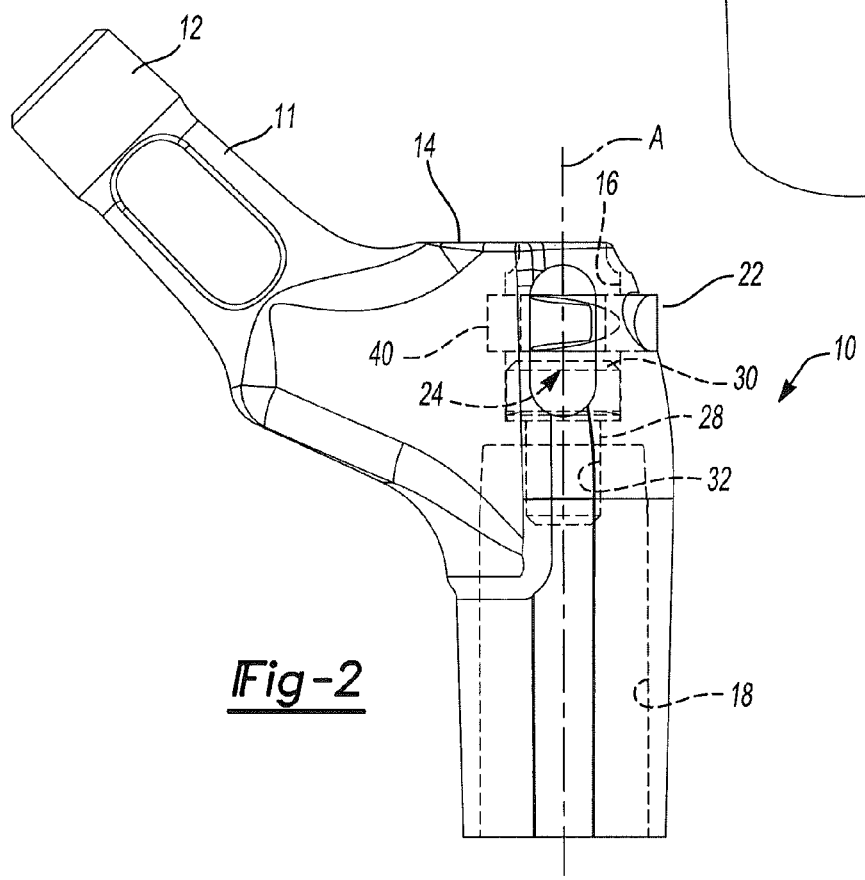
FIG. 2 is a side view of the trial proximal component of FIG. 1.
Figure 3:
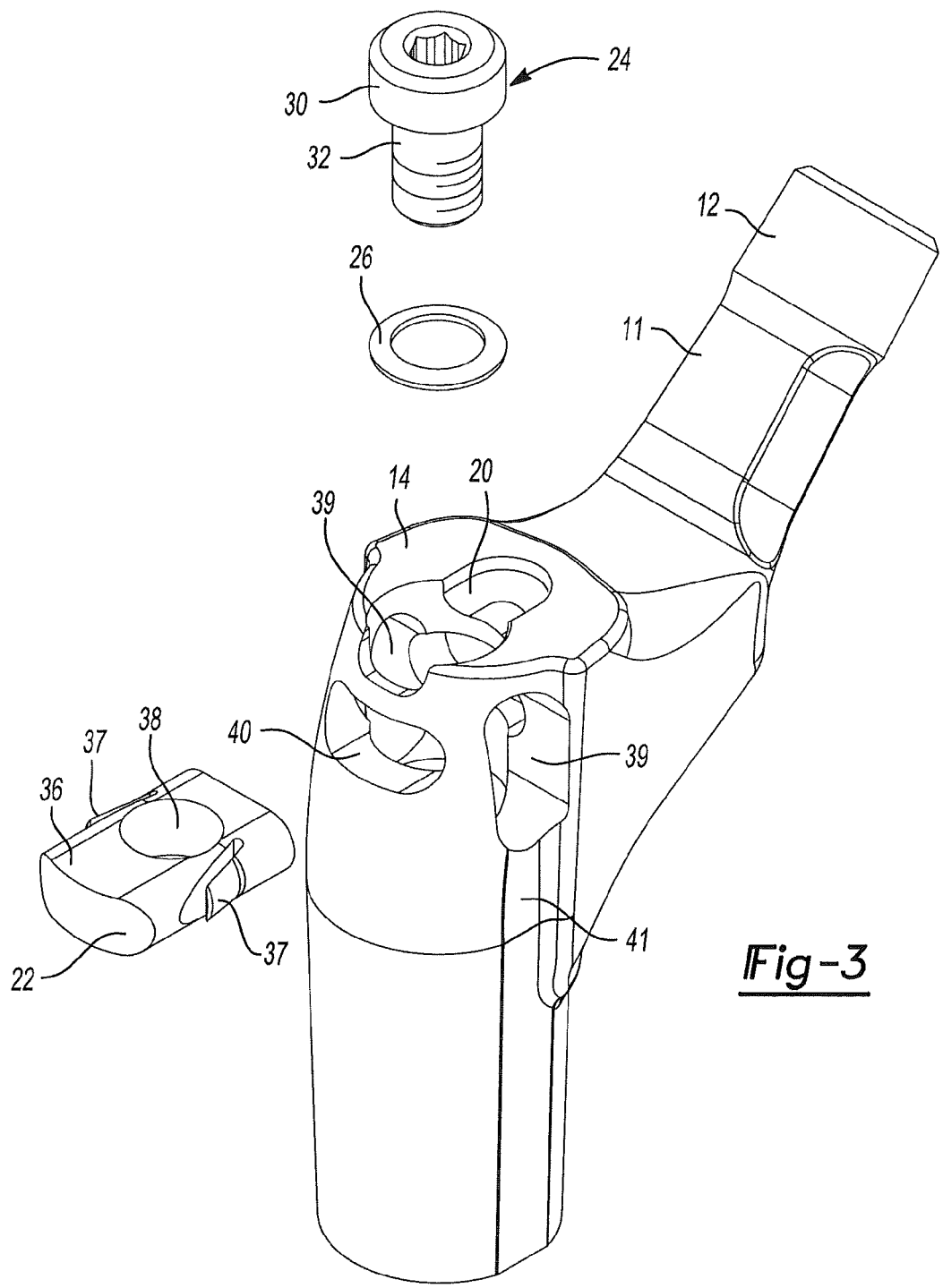
FIG. 3 is an exploded perspective view of the trial proximal component of FIG. 1.

Example embodiments will now be described more fully with reference to the accompanying drawings.

With initial reference to FIGS. 1-4, a trial proximal body 10 for a modular femoral implant according to the present teachings is illustrated at reference numeral 10. The trial proximal body 10 generally includes a neck 11 having a head engagement trunnion 12 and a proximal surface 14. The trial proximal body 10 defines a proximal bore 16 and a distal bore 18 that axially extend through the proximal body 10 along axis A.

The proximal surface 14 includes a keyed or anti-rotation locking portion 20. As illustrated, the locking portion 20 defines a recess within the proximal surface 14. The locking portion 20 can be of any size, shape, or configuration to cooperate with an alignment jig, which is described herein, to prevent the trial proximal body 10 from rotating when it is secured to the alignment jig.

The proximal bore 16 extends from the proximal surface 14 and into the trial proximal body 10. Mounted within the proximal bore 16 are an insert slide 22, a fastener 24, and a washer 26. The proximal bore 16 is connected to the distal bore 18 by an axial passageway 28. The proximal bore 16 is longitudinally and concentrically aligned with the distal bore 18 along the axis A.

The fastener 24 may be any suitable fastener, such as a bolt as illustrated. The fastener 24 includes a head 30 and a threaded stem 32. The fastener 24 is positioned such that the head 30 is seated within the proximal bore 16 and the threaded stem 32 extends through the passageway 28 and into the distal bore 18.

The washer 26 is seated between the head 30 and a bottom surface 34 of the proximal bore 16. The washer 26 can be any suitable washer or device to prevent the head 30 from contacting the bottom surface 34 and promote a rotational friction lock when tightening the fastener 24, such as a spring-type Belleville washer.

Figure 4:
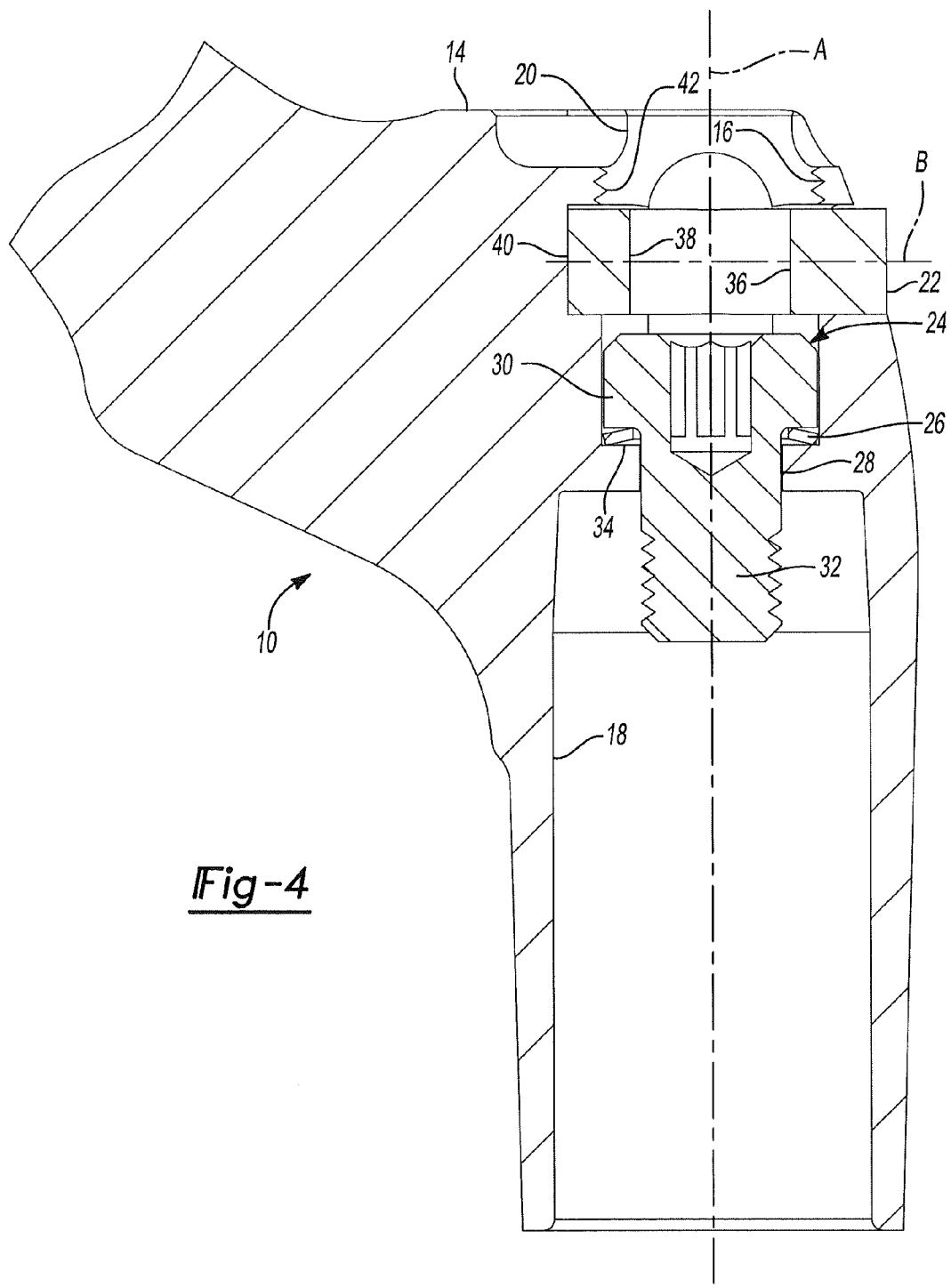
FIG. 4 is a cross-sectional view of the trial proximal component of FIG. 1.

The slide 22 includes a body 36 that defines an aperture 38. The aperture 38 has a diameter of any suitable size that is smaller than both a diameter of the proximal bore 16 and of the head 30. The slide 22 further includes flexible tabs 37 that extend from opposite sides of the body 36. The slide 22 is removably mounted within a slot or transverse bore 40 extending through the proximal bore 16 through interaction between the flexible tabs 37 and openings 39 defined by side portions 41 of the trial proximal body 10. As illustrated in FIG. 4, the slot 40 extends along an axis B that is transverse to the axis A. The head 30 of the fastener 24 is positioned within the proximal bore 16 between the slide 22 and the bottom surface 34. Thus, the slide 22 prevents the fastener 24 from exiting the proximal bore 16 and retains the threaded stem 32 within the passageway 28 and the distal bore 18. A plurality of slides 22 having apertures 38 of various different sizes can be provided to retain fasteners 24 of different sizes. In place of the slide 22, an internal retaining ring can be located within a groove in an interior surface of the proximal bore 16 to retain the fastener 24 in the proximal bore 16. In embodiments that include the internal retaining ring, the distal bore 18 need not be included.

The proximal bore 16 further includes a threaded portion 42 proximate to the proximal surface 14. The threaded portion 42 can be used to mount the trial proximal body 10 to an alignment jig as described herein.

The distal bore 18 is tapered toward the passageway 28, such that it is most narrow at the passageway 28, to provide a locking taper surface. As discussed herein, the distal bore 18 is of any suitable size and shape to receive a trial distal stem and/or a distal stem implant. The distal bore 18 can be tapered along any suitable portion of its length and the degree of taper can vary such that the distal bore 18 tapers to a greater extent proximate to the passageway 28 than distal thereto as illustrated.

The trial proximal body 10 can be provided in a variety of different sizes and shapes corresponding to bone(s) to be repaired. Multiple trial proximal bodies 10 of different sizes and shapes can be provided together in a kit. For example, the multiple trial proximal bodies 10 can have necks 11 and distal bores 18 of various different widths and lengths.

With additional reference to FIGS. 5-6, a trial distal stem according to the present teachings is illustrated at reference numeral 50. The trial distal stem 50 generally includes a first end 52 having a connection region 54 and a second end 56 having a distal tip 58. The first end 52 is opposite to the second end 56. The distal tip 58 can define a notch 59. The portions of the distal tip 58 defining the notch 59 are flexible to relieve pressure at the implant site.

The connection region 54 includes a receptacle 60 that extends within the first end 52. The receptacle 60 is sized and shaped to receive the fastener 24 of the trial proximal body 10. The receptacle 60 includes threads 62 that can cooperate with the threaded stem 32 to secure the fastener 24 within the receptacle 60.

The connection region 54 of the trial distal stem 50 further includes a tapered outer surface 64 at the first end 52. The tapered outer surface 64 extends from the first end 52 to a suitable distance to facilitate reception of the connection region 54 within the distal bore 18 of the trial proximal body 10 and the formation of a taper lock with the distal bore 18. An annular collar 66 extending from an outer diameter of the trial distal stem 50 is provided at a distal end of the connection region 54.

The trial distal stem 50 is curved or bowed from about the collar 66 to the second end 56 to approximate the natural shape of a femur. The trial distal stem 50 can be provided in a variety of different sizes, shapes, and degrees of curvature corresponding to the femur to be repaired. Multiple trial distal stems 50 of different sizes, shapes, and degrees of curvature can be provided together in a kit.

Figure 7:
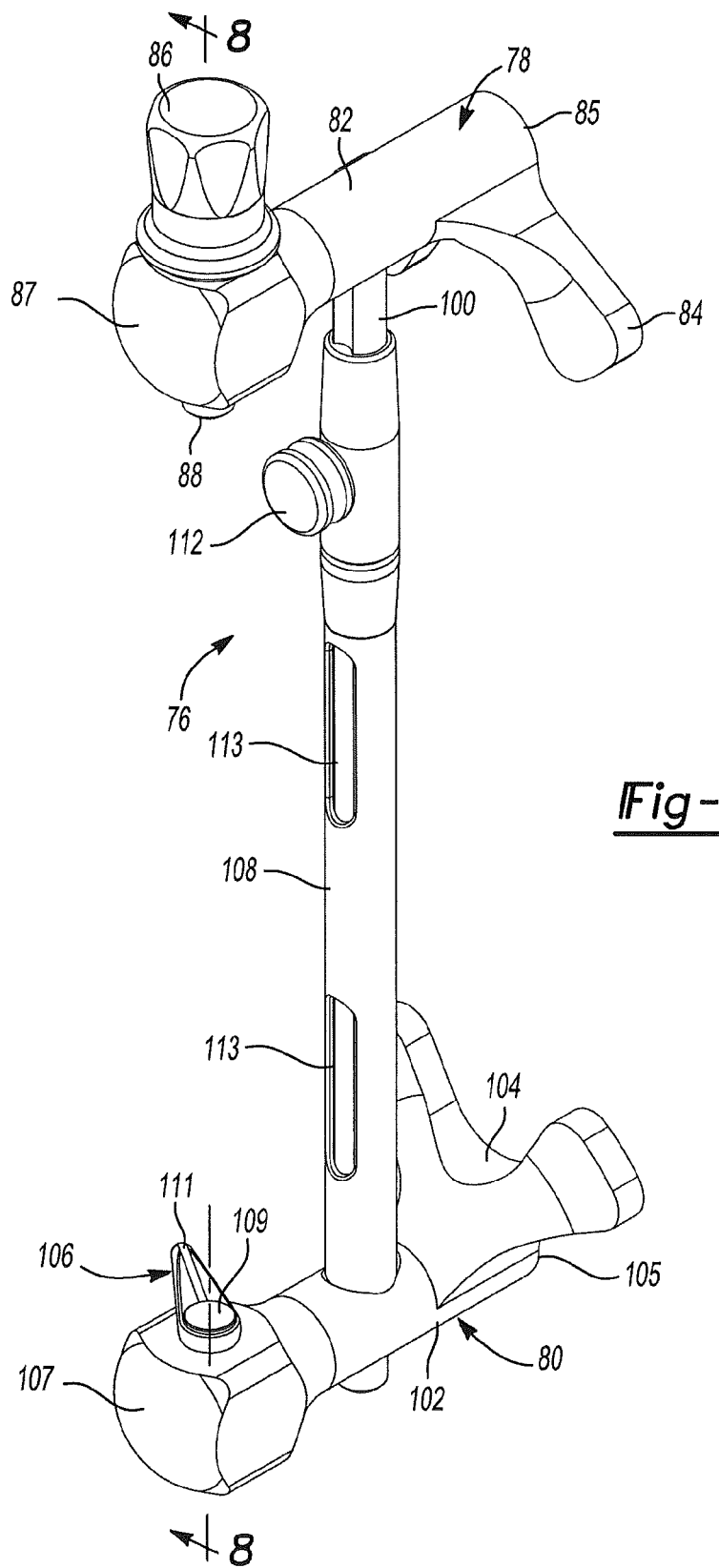
FIG. 7 is a perspective view of an alignment jig assembly according to the present teachings.
Figures 8, 9:
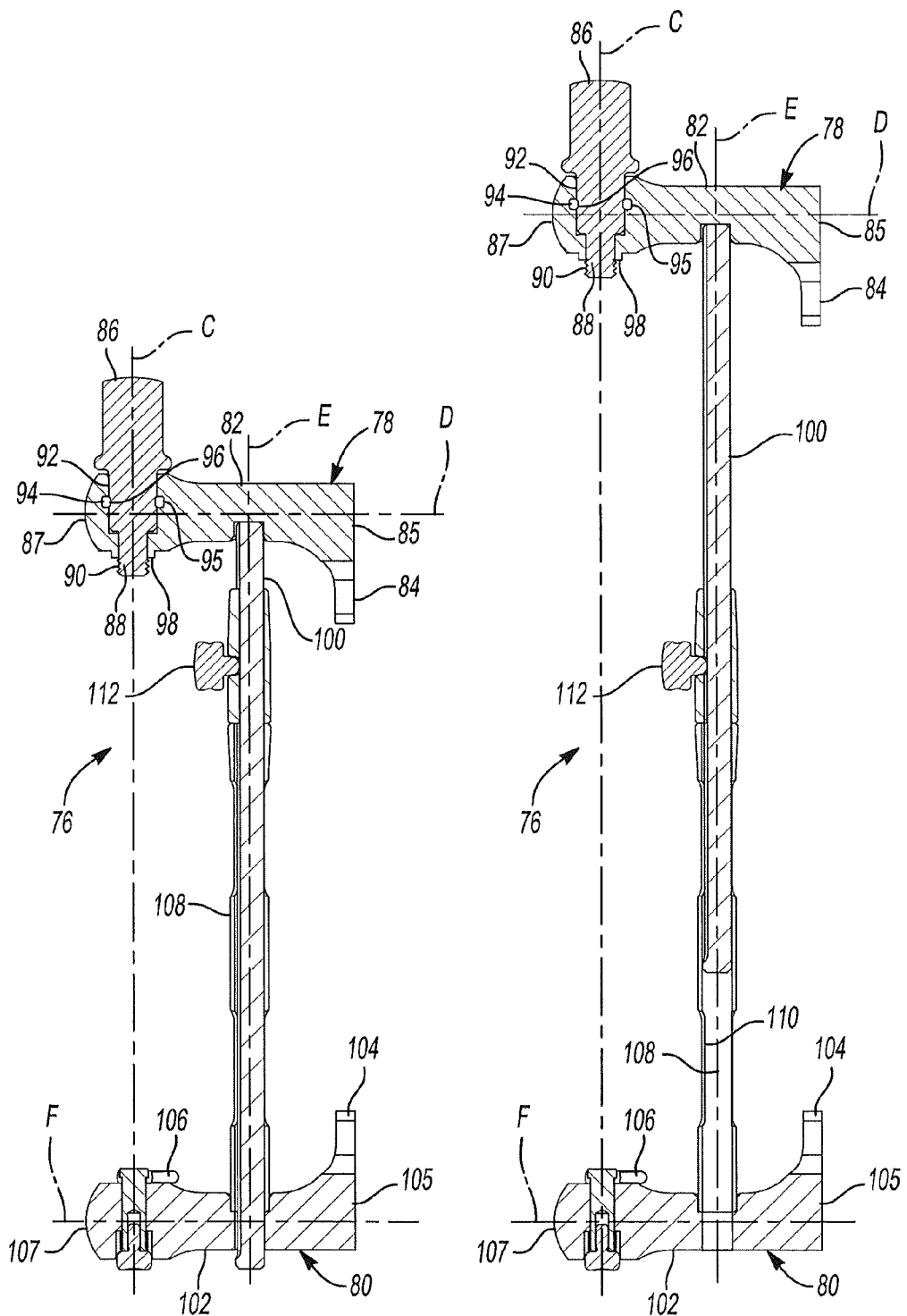
FIG. 8 is a side cross-sectional view of the alignment jig assembly of FIG. 7 in a retracted position.
FIG. 9 is a side cross-sectional view of the alignment jig assembly of FIG. 7 in an expanded position.

With additional reference to FIGS. 7-9, an alignment jig assembly according to the present teachings is illustrated at reference numeral 76. The alignment jig assembly 76 includes a proximal alignment jig portion 78 and a distal alignment jig portion 80.

The proximal alignment jig portion 78 includes an elongated proximal support 82 having a pedestal 84 at a first end 85 and a locking knob 86 at a second end 87 that is opposite to the first end 85. The locking knob 86 includes an engagement shaft 88 having threads 90 that are configured to engage the threaded portion 42 of the trial proximal body 10. The locking knob 86 is seated within a bore 92 that extends through the proximal support 82 and has a longitudinal axis C that is transverse to a longitudinal axis D of the proximal support 82, as illustrated in FIGS. 8 and 9. The bore 92 receives a circular spring or washer 94, such as a split ring washer, in an annular recess 75 of the bore 92. The circular spring or washer 94 engages a depression 96 of the locking knob 86 to secure the locking knob 86 within the bore 92 while permitting rotational movement of the locking knob 86 within the bore 92. Protruding from the proximal support 82 proximate to where the engagement shaft 88 extends from the bore 92 is an engagement member 98 that is sized and shaped to engage the locking portion 20 of the trial proximal body 10 to prevent rotation of the trial proximal body 10 when it is mounted to the proximal alignment jig portion 78. In this regard, the engagement member 98 nests within the locking portion 20 to restrict rotation of the trial proximal body 10 relative to the proximal alignment jig portion 78.

A proximal support rod 100 extends from the proximal support 82 between the pedestal 84 and the locking knob 86. The proximal support rod 100 extends along a longitudinal axis E that is perpendicular to a longitudinal axis D of the proximal support 82, as illustrated in FIGS. 8 and 9. The proximal support rod 100 connects the proximal alignment jig portion 78 to the distal alignment jig portion 80, as further discussed herein.

The distal alignment jig portion 80 includes an elongated distal support 102 having a pedestal 104 at a first end 105 and an alignment tab 106 at a second end 107 that is opposite to the first end 105. The alignment tab 106 includes a center portion 109 and a tip portion 111 extending therefrom. The alignment tab 106 is rotationally mounted to the distal support 102 at the center portion 109, which is generally vertically aligned with the locking knob 86 of the proximal alignment jig portion 78 along the axis C.

A distal support rod 108 extends from the distal support 102 between the pedestal 104 and an alignment tab 106. The distal support rod 108 extends along the longitudinal axis E, which is perpendicular to a longitudinal axis F of the distal support 102. The distal support rod 108 defines a central cavity 110 sized to slidably and coaxially receive the proximal support rod 100 to restrict rotational movement there between. The distal support rod 108 defines windows 113 that permit access to an interior of the distal support rod 108.

The distal support rod 108 further includes a locking tab 112 that engages the proximal support rod 100 to lock the proximal and distal support rods 100 and 108 together, and consequently the proximal and distal alignment jig portions 78 and 80 together as well. The locking tab 112 can engage the proximal support rod 100 at nearly any position along its length, thereby permitting the proximal alignment jig portion 78 and the distal alignment jig portion 80 to be moved closer together (FIG. 8) or farther apart (FIG. 9) as necessary to accommodate various different sizes of the trial proximal body 10 and the trial distal stem 50.

With additional reference to FIGS. 10-14, an exemplary method of using the trial proximal body 10, the trial distal stem 50, and the alignment jig assembly 76 is illustrated. While the method is described with respect to the repair of a femur 150, the present teachings can be used to repair a variety of other suitable bones as well, particularly bones having a curved or bowed stem.

Figure 10:
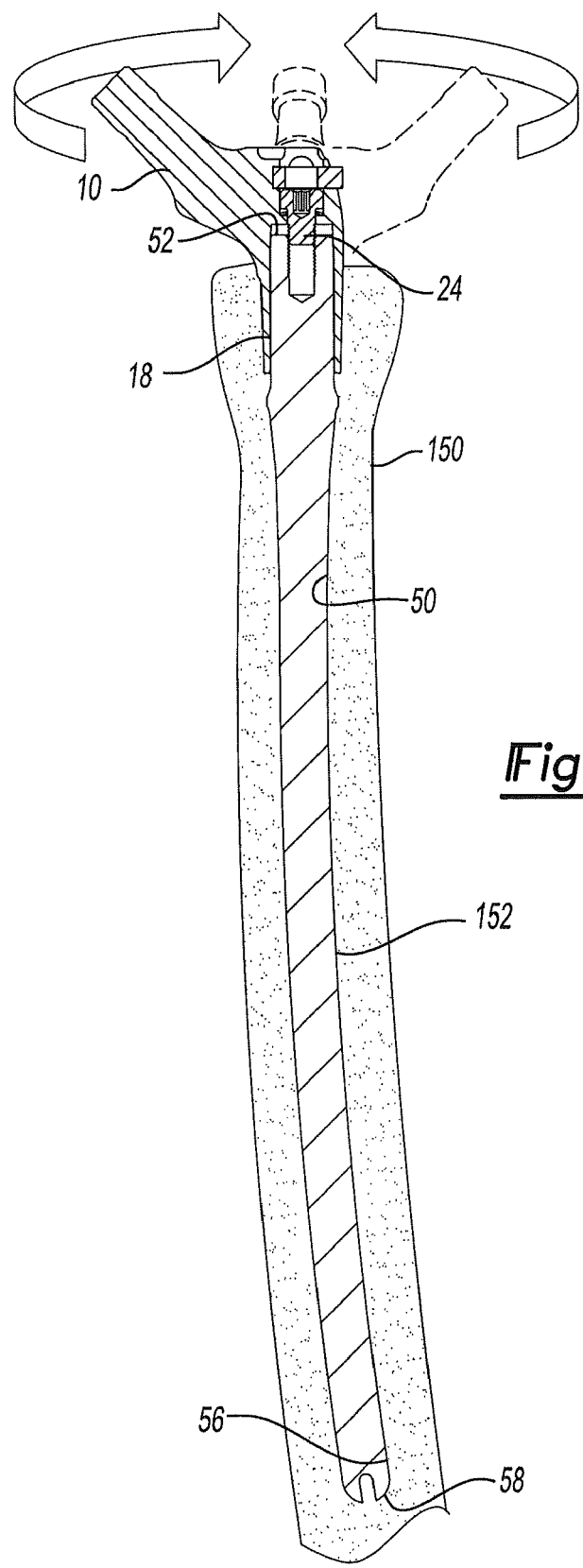
FIG. 10 is a side cross-sectional view of the trial proximal component loosely mounted to the trial distal stem to permit rotational movement therebetween for trialing, the trial distal stem is seated in a femur.
Figure 11:
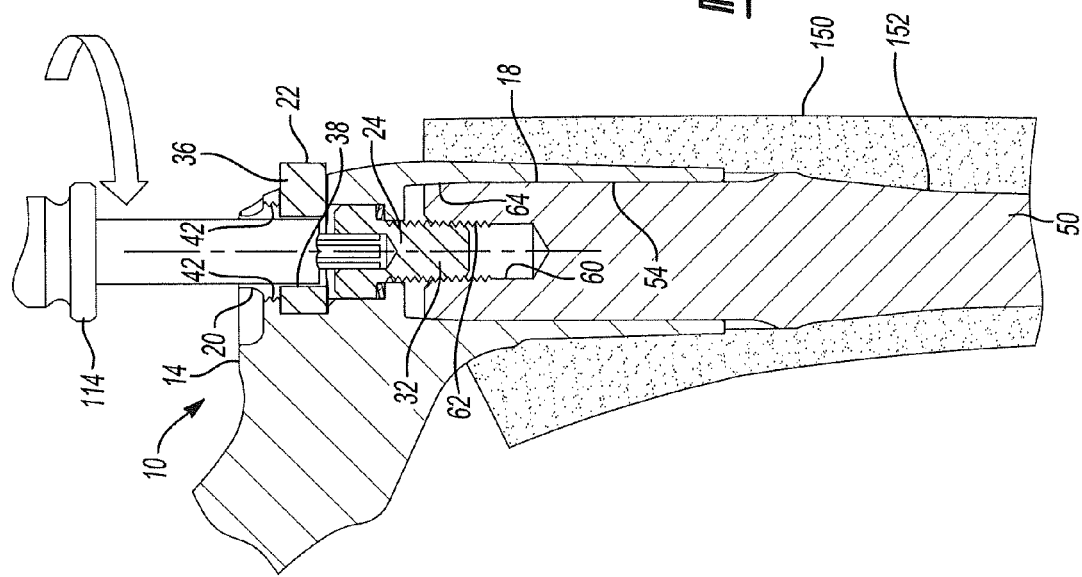
FIG. 11 is a side cross-sectional view of the trial proximal component loosely mounted to the trial distal stem to permit rotational movement therebetween for trialing.
Figure 12:
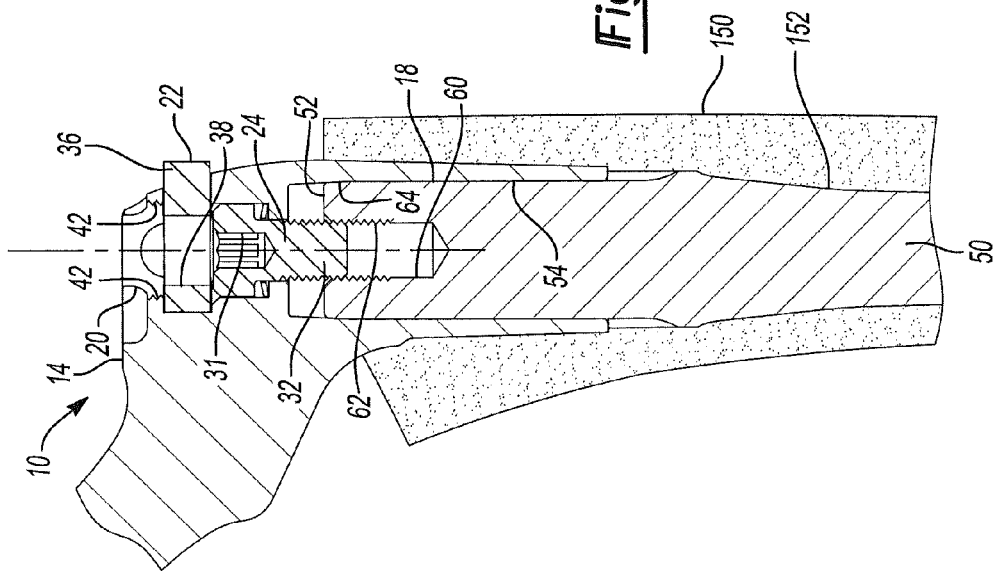
FIG. 12 is a side cross-sectional view of the trial proximal component mounted to the trial distal stem, a tool is illustrated in cooperation with a fastening device of the trial proximal component to tighten the fastening device and restrict rotation between the trial proximal component and the trial distal stem.

With initial reference to FIGS. 10 and 11, the first end 52 of the trial distal stem 50 is inserted within the distal bore 18 of the trial proximal body 10 and is secured therein by tightening the fastener 24 with a suitable tool 114 engaging a bore 31 of the fastener 24 (FIG. 11), such that the threaded stem 32 of the fastener 24 partially engages the threads 62 of the trial distal stem 50. The fastener 24 is not completely tightened in order to permit rotational movement (illustrated in phantom in FIG. 10) between the trial proximal body 10 and the trial distal stem 50 during trialing.

An intramedullary canal 152 of the femur 150 is prepared, such as by reaming, and the trial distal stem 50 is inserted therein. As the trial distal stem 50 is inserted it rotates such that the curvature of the trial distal stem 50 matches the curvature of the intramedullary canal 152 and the overall curvature of the femur 150. The trial proximal body 10 is then rotated to a desired position determined from trialing, as illustrated in phantom in FIG. 10. With additional reference to FIG. 12, to preserve the orientation of the trial proximal body 10 relative to the trial distal stem 50, the fastener 24 is further tightened using the tool 114 so that the tapered outer surface 64 of the trial distal stem 50 engages the tapered portion of the distal bore 18 proximate to the passageway 28 to form a mating taper therebetween and prevent further rotation of the trial proximal body 10 to the trial distal stem 50.

Figure 13:
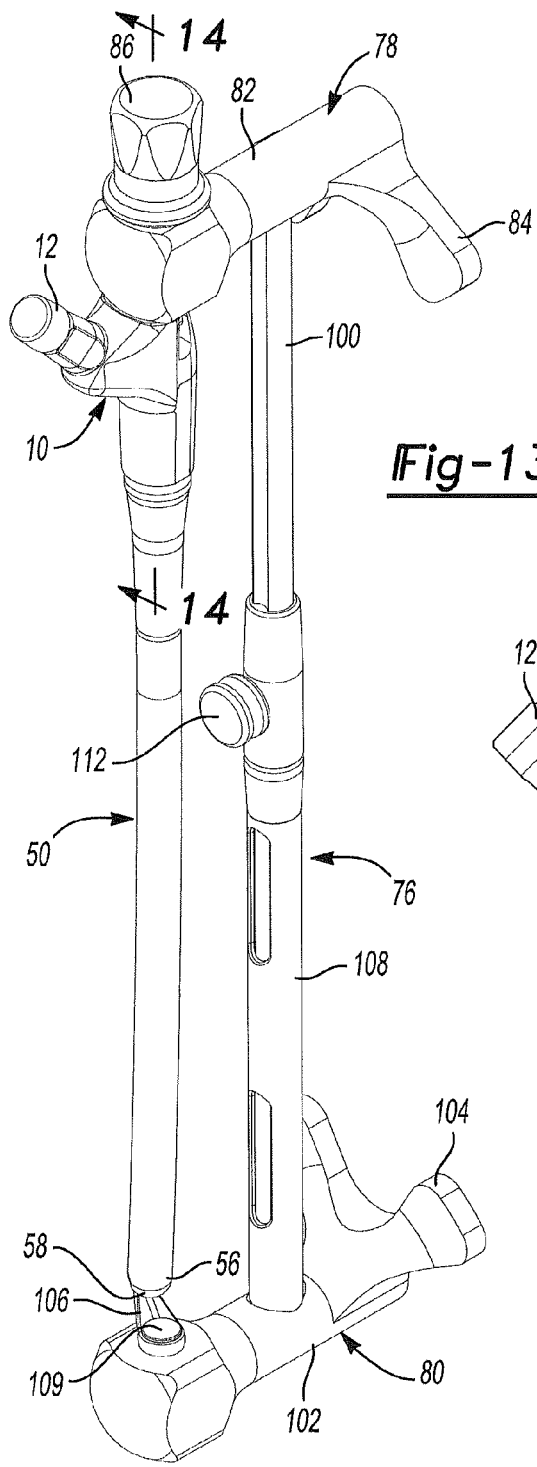
FIG. 13 is a perspective view of the trial proximal component and the trial distal stem connected together and mounted to the alignment jig assembly to identify the orientation of the trial distal stem relative to the trial proximal component.
Figure 14:
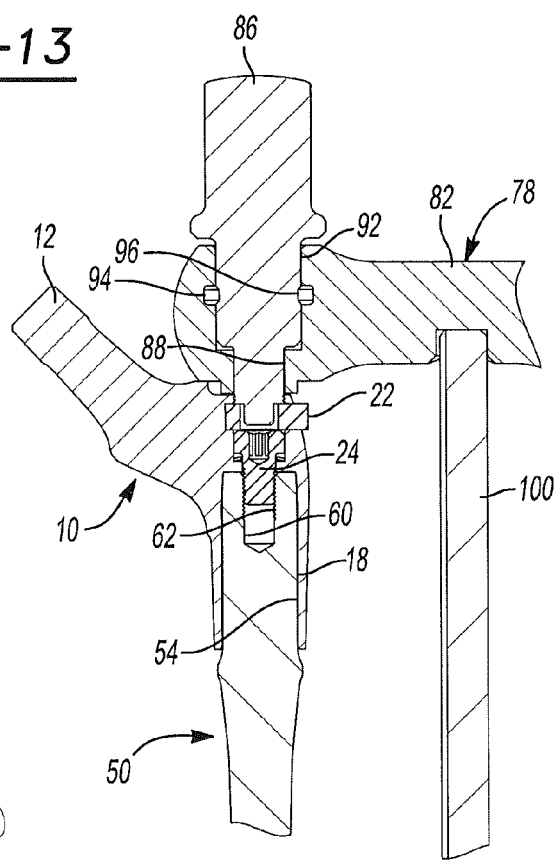
FIG. 14 is a cross-sectional view taken along line 14-14 of FIG. 13.

The trial proximal body 10 and the trial distal stem 50 locked thereto are removed from contact with the femur 150 and connected to the alignment jig assembly 76 to measure the relative positions of each. As illustrated in FIGS. 13 and 14, the trial proximal body 10 is mounted to the proximal alignment jig portion 78 through cooperation between the threads 90 of the engagement shaft 88 and the threaded portion 42 of the trial proximal body 10. The engagement member 98 of the proximal alignment jig portion 78 cooperates with locking portion 20 of the trial proximal body 10 to prevent rotation therebetween. The distance between the proximal and distal alignment jig portions 78 and 80 is set such that the distal tip 58 is level with the alignment tab 106 and the locking tab 112 is tightened to secure the proximal and distal alignment jig portions 78 and 80 in relative position to each other. The alignment tab 106 is rotated such that it contacts the distal tip 58 or is just distal to the distal tip 58 to mark the relative position of the distal tip 58 and curvature of the trial distal stem 50, which corresponds to the natural curvature of the femur 150 determined during trialing.

With the alignment jig assembly 76 set, the trial proximal body 10 and the trial distal stem 50 are removed from the alignment jig assembly 76. For example, the locking tab 112 can be loosened to permit further separation of the proximal and distal alignment jig portions 78 and 80, thereby opening the alignment jig assembly 76. The locking knob 86 is rotated to disengage the threaded portion 42 and permit separation of the trial proximal body 10 from the proximal alignment jig portion 78. The trial distal stem 50 can be removed from engagement with the trial proximal body 10 by unscrewing the fastener 24 from engagement with the trial distal stem 50. As the fastener 24 is unscrewed it contacts the slide 22 to provide a counterforce against the fastener 24 and assist with the separation of the trial distal stem 50 from the trial proximal body 10 by disrupting the taper connection between the distal bore 18 and the tapered outer surface 64 of the trial distal stem 50. In other words, rotation of the fastener 24 biased against the slide 22 pushes the trial distal stem 50 out from within the distal bore 18 of the trial proximal body 10.

As illustrated in FIGS. 15 and 16, a proximal body implant 176 is mounted to the proximal alignment jig portion 78. The proximal body implant 176 is similar to the trial proximal body 10 in both size and shape. Further, the interior of the proximal body implant 176 does not include the fastener 24. The proximal body implant 176 does include a proximal bore 180 having a threaded portion 182 and a distal bore 184 having a tapered interior surface 186. A proximal surface 188 includes a locking member 190 that is configured to mate with the engagement member 98 of the proximal alignment jig portion 78.

The proximal body implant 176 is mounted to the proximal support 82 through cooperation between the threads 90 of the engagement shaft 88 and the threaded portion 182 of the proximal bore 180. Cooperation between the locking member 190 and engagement member 98 rotationally aligns the proximal body implant 176 in the same orientation as the trial proximal body 10 and prevents rotational movement of the proximal body implant 176.

Numeral 200 references a distal stem implant. The distal stem implant 200 is substantially similar to the trial distal stem 50. Features of the distal stem implant 200 that are similar to the trial distal stem 50 are designated with the same reference numbers, but further include the prime (') designation. The portion of the distal stem implant 200 between the collar 66' and the second end 56' has a diameter that is generally larger than that of the trial distal stem 50.

With the proximal body implant 176 still mounted to the alignment jig assembly 76, the distal stem implant 200 is rotated such that its second end 56' is aligned with the previously set alignment tab 106 to provide the distal stem implant 200 with the same orientation as the trial distal stem 50. The second end 56' can directly contact the alignment tab 106 or extend proximate thereto depending on its length. The connection region 54' is inserted within the distal bore 184 to form a taper lock therein and secure the distal stem implant 200 to the proximal body implant 176 in the same orientation achieved between the trial proximal body 10 and the trial distal stem 50.

Figure 17:
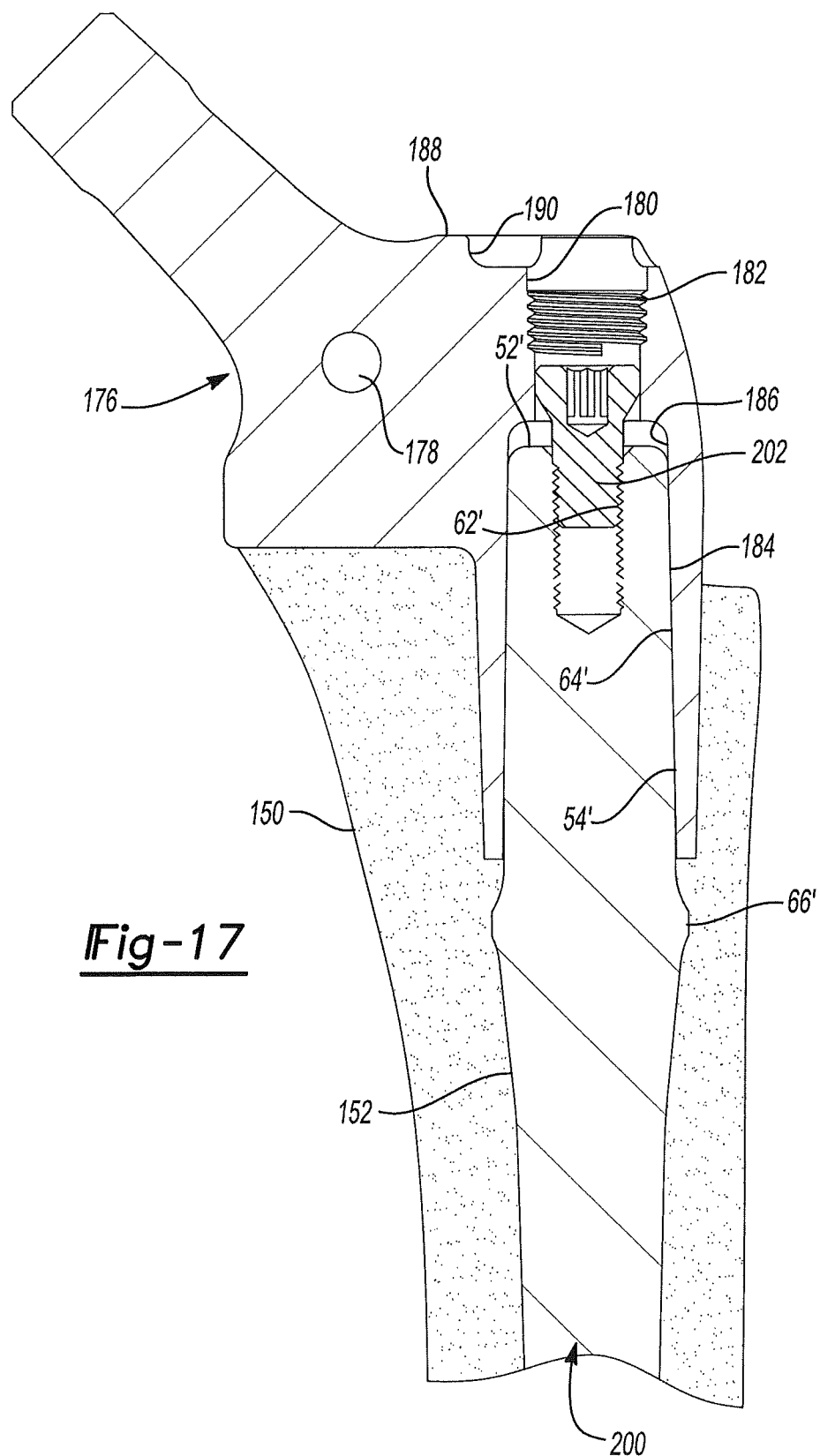
FIG. 17 is a side cross-sectional view of the distal stem implant and the proximal body implant implanted in the femur.

The proximal body implant 176 and the distal stem implant 200 are removed from the alignment jig assembly 76 and then further secured together using any suitable device, such as by tightening a screw 202 seated in the proximal bore 180 of the proximal body implant 176 within the threads 62' of the distal stem implant 200 and/or with an impactor. The distal stem implant 200 is implanted and secured in the intramedullary canal 152 (FIG. 17) in any suitable manner. As a result of the alignment performed using the alignment jig assembly 76, the distal stem implant 200 and the proximal body implant 176 are implanted in the femur 150 in the same orientation set between the trial proximal body 10 and the trial distal stem 50 during trialing.

The proximal body implant 176 and the distal stem implant 200 can be of any suitable size or shape to repair the femur 150. For example, the proximal body implant 176 and the distal stem implant 200 can be selected from a kit having multiple proximal body implants and multiple distal stem implants of various different sizes and shapes.

Figure 18:
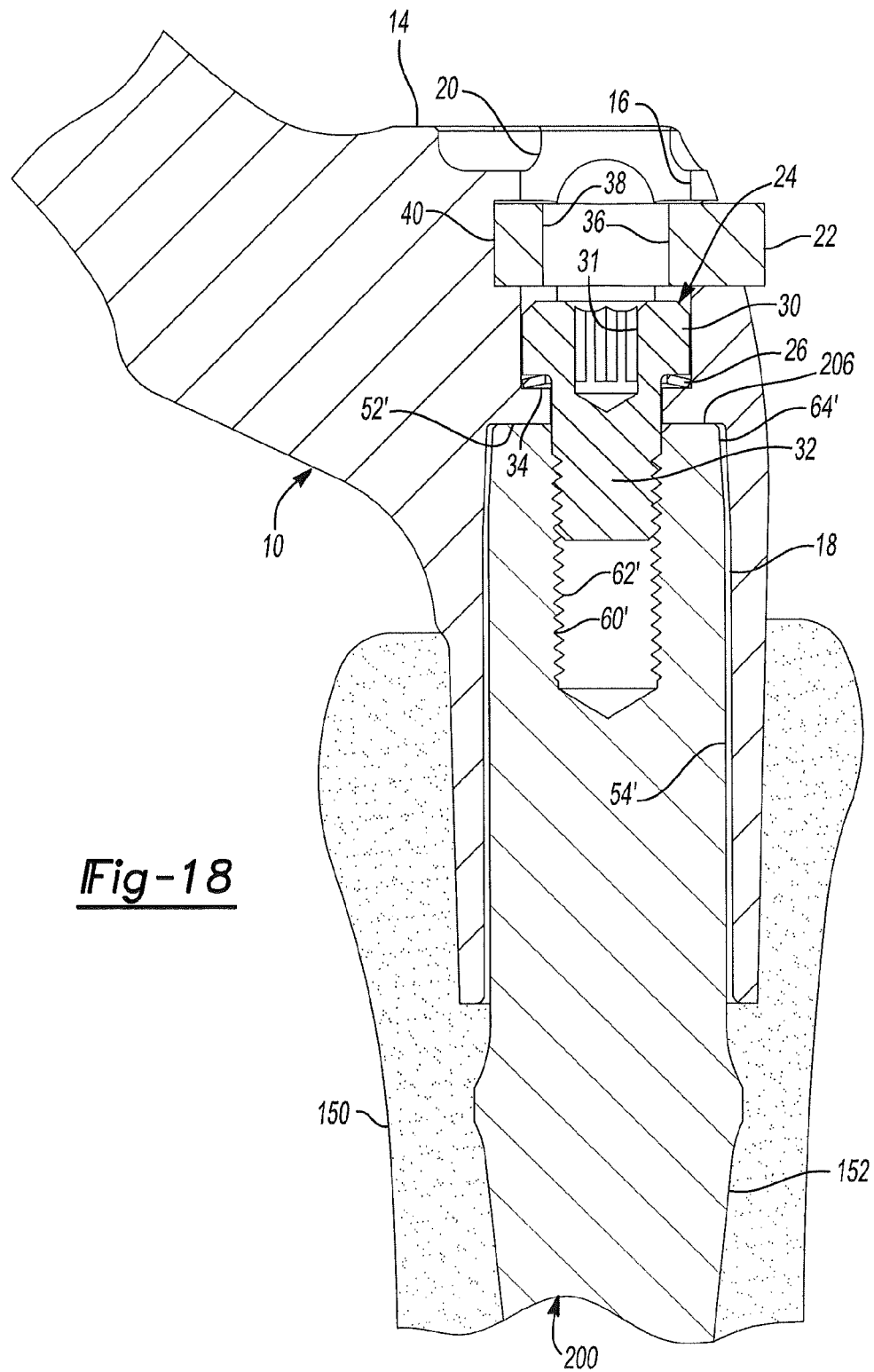
FIG. 18 is a side cross-sectional view of the trial proximal component mounted to the distal stem implant inserted within the femur.

With additional reference to FIG. 18, an additional method according to the present teachings is illustrated. As illustrated, the trial proximal body 10 can be mounted to the distal stem implant 200 with the distal stem implant 200 implanted in the femur 150. The distal stem implant 200 is inserted within the intramedullary canal 152 and follows the natural shape of the intramedullary canal 152. The trial proximal body 10 is mounted thereto through cooperation between the fastener 24 and the threads 62' of the receptacle 60'. The connection region 54' of the distal stem implant 200 has a smaller tapered outer surface 64' than the tapered outer surface 64 of the trial distal stem 50. Thus, the first end 52' mates with a proximal end 206 of the distal bore 18 to provide rotational stability between the distal stem implant 200 and the trial proximal body 10 through friction. The washer 26 biases the fastener 24 upward toward the proximal surface 14 to increase the friction between the first end 52' and the proximal end 206 of the distal bore 18 to increase the rotational stability. The trial proximal body 10 can be used for trialing and joint reduction. After the desired orientation of the trial proximal body 10 has been set, the position of the trial proximal body 10 is recorded in any suitable manner, such as by marking the position on the femur 150 and/or through visualization, in order to recreate the same orientation with the proximal body implant 176.

Figure 19:
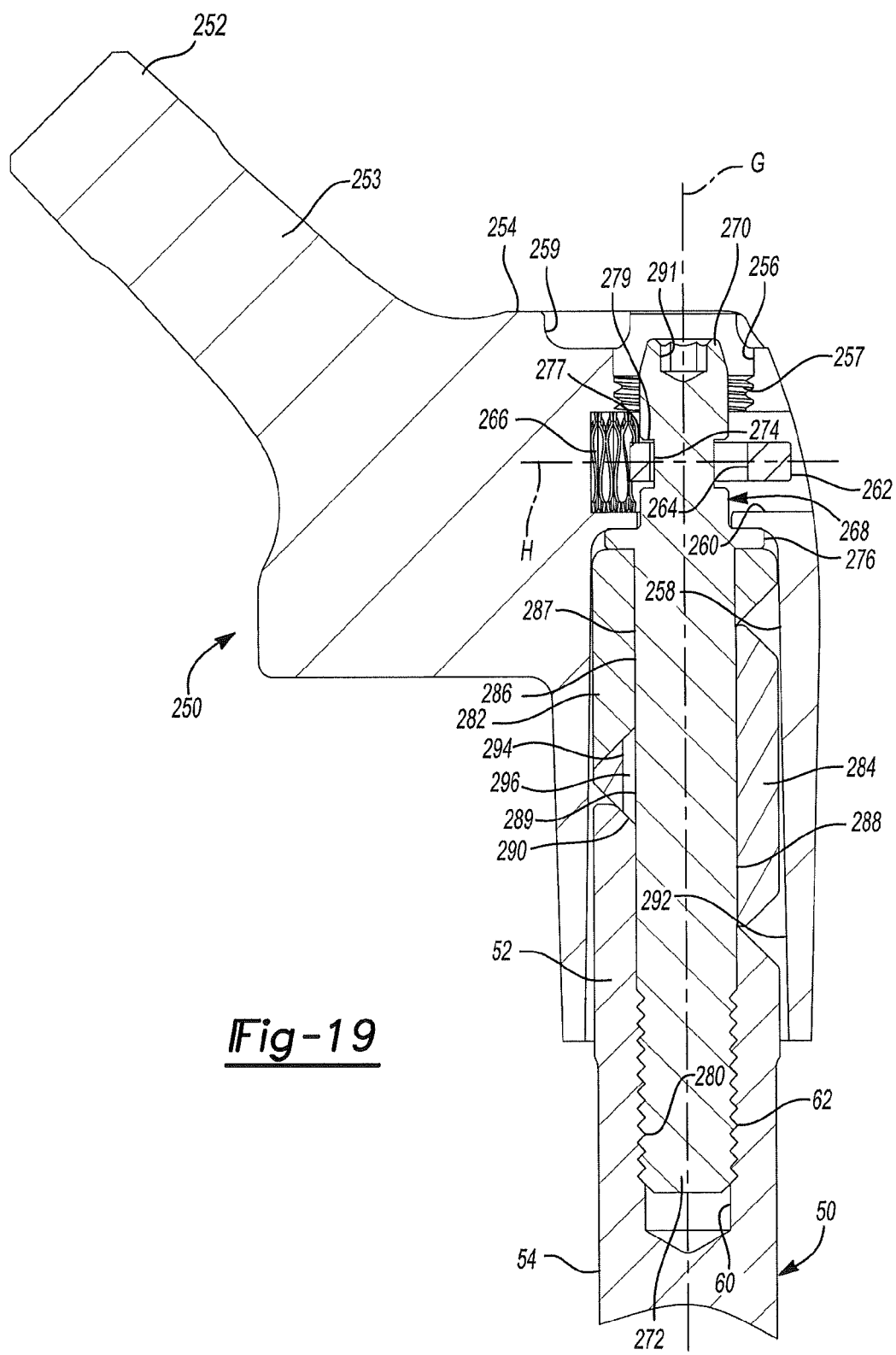
FIG. 19 is a side cross-sectional view of an additional embodiment of a trial proximal component according to the present teachings.
Figure 20:
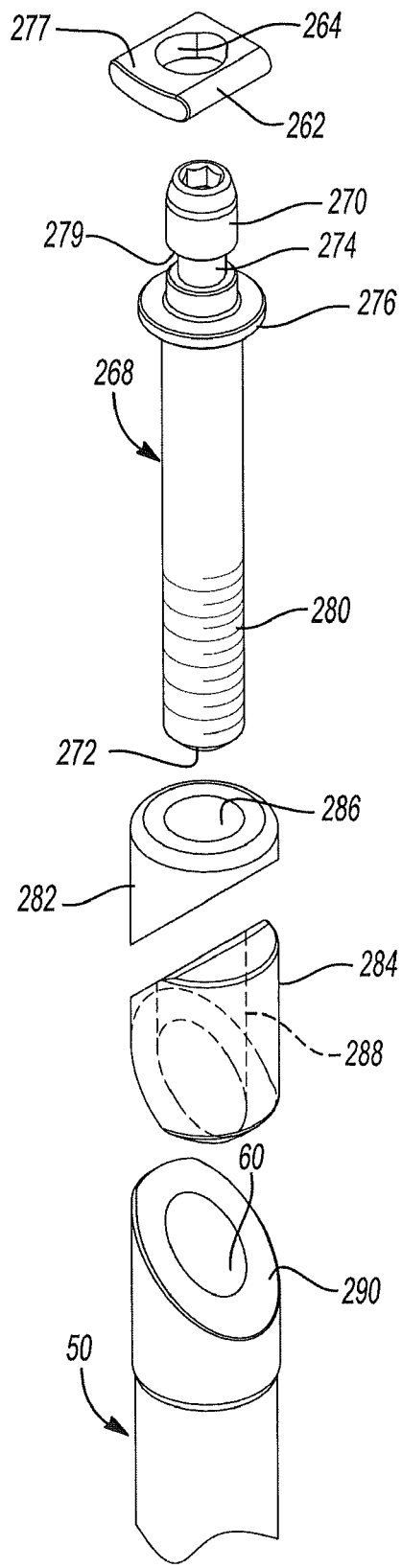
FIG. 20 is an exploded perspective view of a locking rod, a proximal locking wedge, and a distal wedge of the trial proximal component of FIG. 19, as well as a proximal portion of an additional embodiment of a trial distal stem according to the present teachings.

With additional reference to FIGS. 19 and 20, a trial proximal body 250 having an alternate locking mechanism for fastening the trial distal stem 50 thereto is illustrated. The trial proximal body 250 generally includes a head engagement flange 252 extending from a neck 253, a proximal surface 254, a proximal bore 256, and a distal bore 258. The proximal bore 256 and the distal bore 258 axially extend through the trial proximal body 250 along an axis G.

The proximal surface 254 includes a locking portion 259 that is similar to the locking portion 20 and can be of any size, shape, or configuration to cooperate with the engagement member 98 of the alignment jig assembly 76 to restrict rotational movement.

The proximal bore 256 extends from the proximal surface 254 and into the trial proximal body 250. The proximal bore 256 includes threads 257 operable to mate with threads 90 of the locking knob 86 of the alignment jig assembly 76. A slot or transverse bore 260 extends through the proximal bore 256 along a longitudinal axis H that is transverse to the longitudinal axis G of the proximal bore 256. Seated within the transverse bore 260 is a button 262 having a center aperture 264. A spring 266 is mounted within the transverse bore 260 and applies pressure to the button 262 along the longitudinal axis of the transverse bore 260 to bias the button 262 away from the transverse bore 260.

A locking rod 268 extends between the proximal bore 256 and the distal bore 258. The locking rod 268 generally includes a first end 270, a second end 272, a neck portion 274, and a shoulder portion 276. The locking rod 268 is positioned such that the neck portion 274 is aligned along the longitudinal axis H of the transverse bore 260. The neck portion 274 is positioned within the center aperture 264 of the button 262 such that a surface 277 (FIG. 20) of the button 262 abuts a flange 279 of the neck portion 274 to prevent the locking rod 268 from exiting the proximal bore 256. The spring 266 maintains the connection between the button 262 and the locking rod 268. The shoulder portion 276 prevents the locking rod 268 from moving further into the proximal bore 256. The second end 272 of the locking rod 268 includes a threaded portion 280.

Mounted within the distal bore 258 is a proximal locking wedge 282 and a distal locking wedge 284. The proximal locking wedge 282 defines a first center bore 286 and the distal locking wedge 284 defines a second center bore 288. The proximal locking wedge 282 and the distal locking wedge 284 are positioned such that the locking rod 268 extends through both the first center bore 286 and the second center bore 288.

The first center bore 286 has an inner diameter 287 that is substantially similar to an outer diameter 289 of the locking rod 268, such that there is little or no transverse movement relative to the axis G between the proximal locking wedge 282 and the locking rod 268. The second center bore 288 has an inner diameter 294 that is larger than the outer diameter 289 of the locking rod 268, thereby defining a gap 296 between the distal locking wedge 284 and the locking rod 268. The gap 296 permits transverse movement relative to the axis G of the distal locking wedge 284 relative to the locking rod 268.

When used in conjunction with the trial proximal body 250, the first end 52 of the trial distal stem 50 includes an angled surface 290. Thus, the first end 52 of the trial distal stem 50 serves as a locking wedge, as further described below.

To connect the trial proximal body 250 to the trial distal stem 50, the second end 272 of the locking rod 268 is inserted within the receptacle 60 such that the threads 280 of the locking rod 268 cooperate and engage the threads 62 of the receptacle 60. The locking rod 268 is rotated using any suitable driving device, such as the tool 114 in cooperation with the bore 291, to draw the first end 52 of the trial distal stem 50 within the distal bore 258.

To achieve a rotational lock between the trial distal stem 50 and the trial proximal body 250, the locking rod 268 is rotated to draw the angled surface 290 of the trial distal stem 50 into contact with the distal locking wedge 284. As the trial distal stem 50 is drawn further into the distal bore 258, the angled surface 290 pushes the distal locking wedge 284 outward against a sidewall 292 of the distal bore 258 to create a rotational friction lock between the distal locking wedge 284 and the sidewall 292, as well as between the distal locking wedge 284 and the trial distal stem 50 to rotationally lock the trial distal stem 50.

The orientation of the trial proximal body 250 and the trial distal stem 50 can be noted using the alignment jig assembly 76 in the same manner described above. In addition to engaging the trial distal stem 50, the trial proximal body 250 can also be mounted to the distal stem implant 200 for use in trialing and joint reduction by providing the distal stem implant 200 with an angled surface that is similar to the angled surface 290 of the trial distal stem 50.

Figure 22:
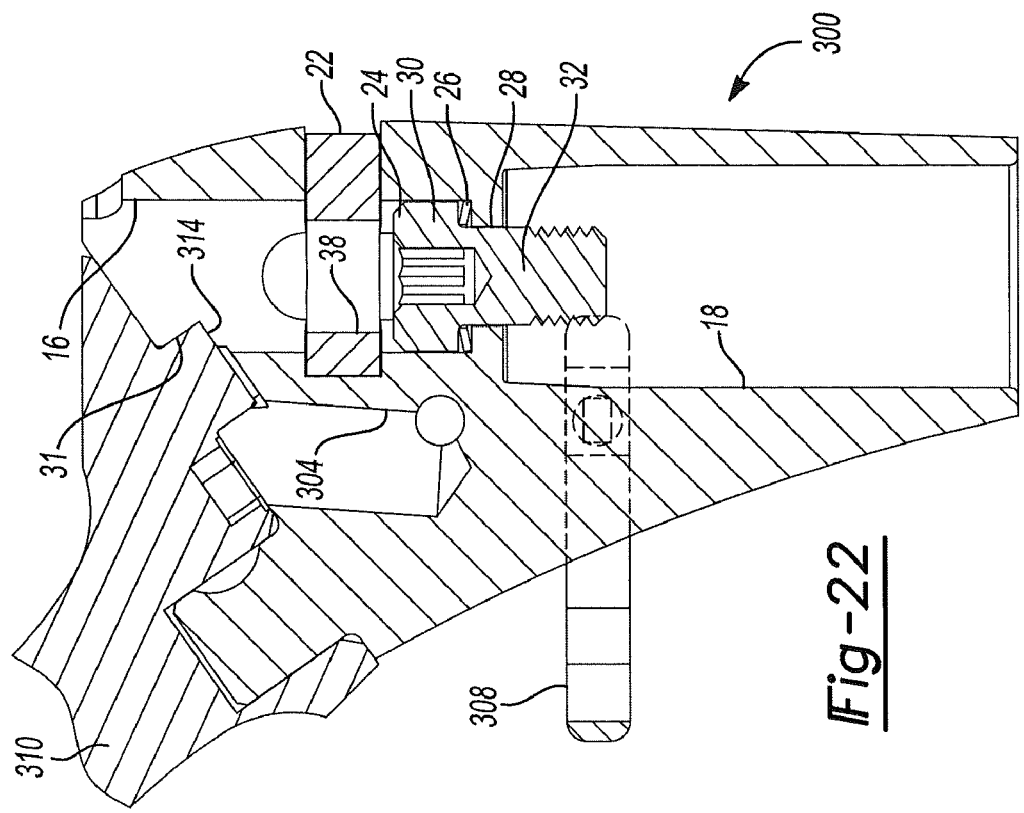
FIG. 22 is a cross-sectional view of the broach of FIG. 21.
Figure 21:
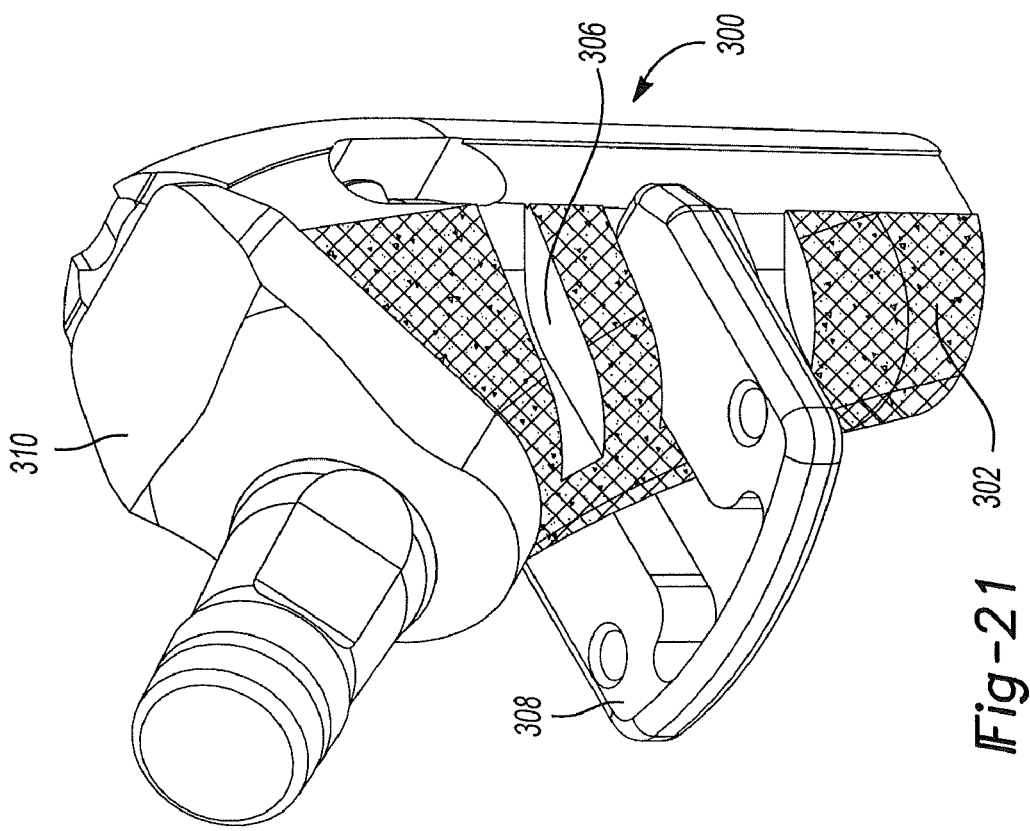
FIG. 21 is a perspective view of a broach according to the present teachings.
Figure 23:
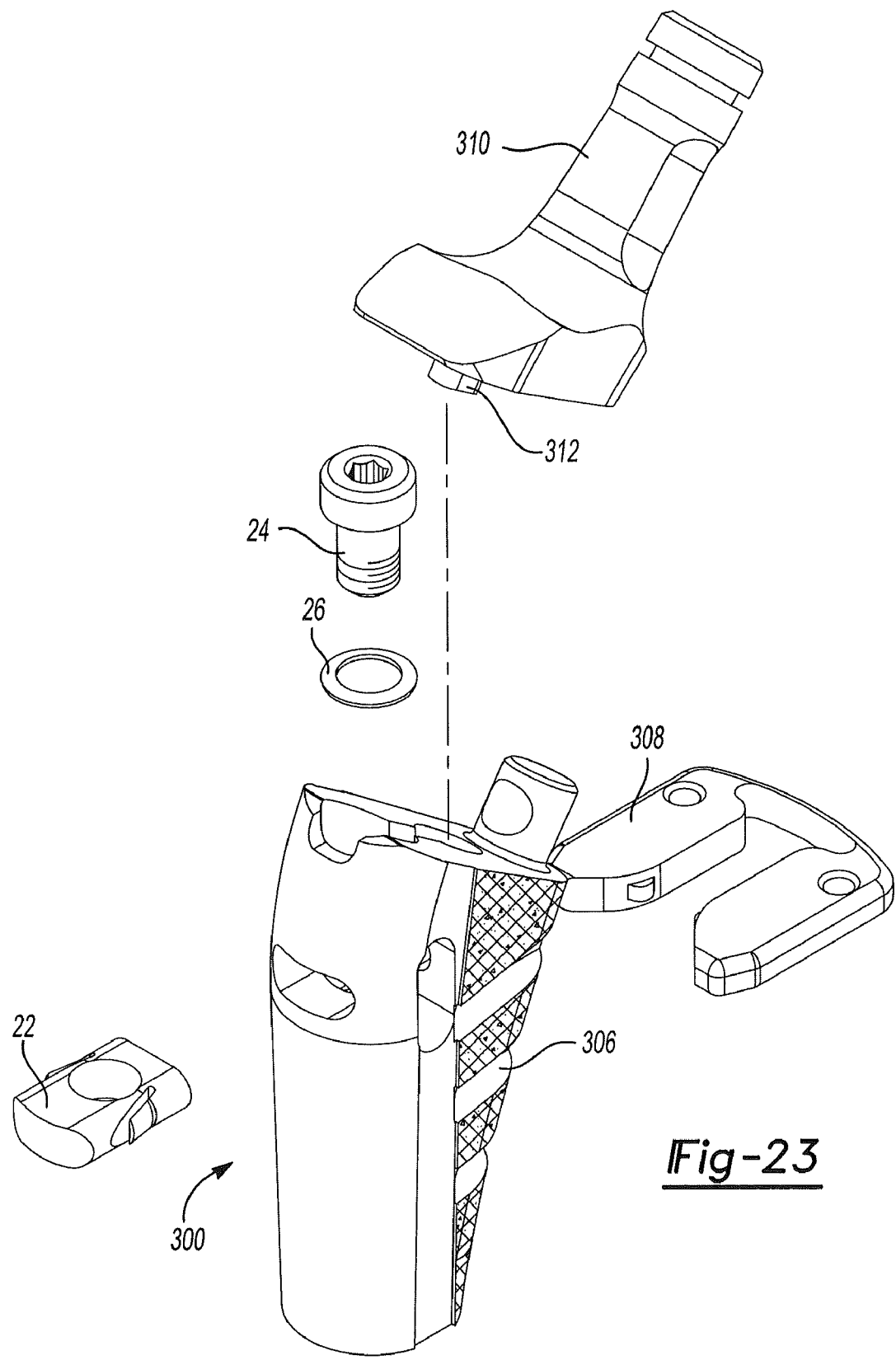
FIG. 23 is an exploded view of the broach of FIG. 21.

With additional reference to FIGS. 21-23, a broach 300 according to the present teachings is illustrated at reference numeral 300. The broach 300 includes an interior engagement and locking mechanism that is substantially similar to the trial proximal body 10. Thus, interior engagement and locking features of the broach 300 that are similar to the interior engagement and locking features of the trial proximal body 10 are designated using the same reference numbers.

An exterior of the broach 300 includes a plurality of cutting teeth 302. A bore 304 is provided and is operable to receive a broach handle (not shown) to facilitate positioning of the broach 300. A plurality of slots 306 are spaced apart along the exterior of the broach 300 and are each sized to receive a calcar platform 308.

A neck trial assembly 310 can be mounted to the broach 300 for use during joint trialing. The neck trial assembly 310 has a locking tab 312 extending therefrom that is sized to be received in a recess 314 to secure the neck trial assembly 310 to the broach.

The broach 300 operates in substantially the same manner as the trial proximal body 10 does. Therefore, the above description of the trial proximal body 10 also applies to the broach 300. For example, the broach 300 is loosely mounted to the trial distal stem 50 using fastener 24 and then trialed in the femur 150 to determine the proper orientation of the broach 300. As the broach 300 is inserted into the femur 150 the cutting teeth 302 of the broach 300 can be used to prepare the proximal femur and the surrounding areas. Use of the broach 300 for preparing the femur 150 and surrounding areas is further described in U.S. patent application Ser. No. 12/718,026, entitled "REVISION BROACH WITH SMOOTH LATERAL SIDE," which is concurrently filed herewith and is incorporated herein by reference. After the proper orientation of the broach 300 with respect to the trial distal stem 50 is set, the fastener 24 is tightened to restrict rotation between the broach 300 and the trial distal stem 50.

The broach 300 and the trial distal stem 50 are then mounted to the alignment jig assembly 76 to record the orientation of the trial distal stem 50 relative to the broach 300. This orientation is then recreated with the proximal body implant 176 and the distal stem implant 200 as described above.

Figure 24:
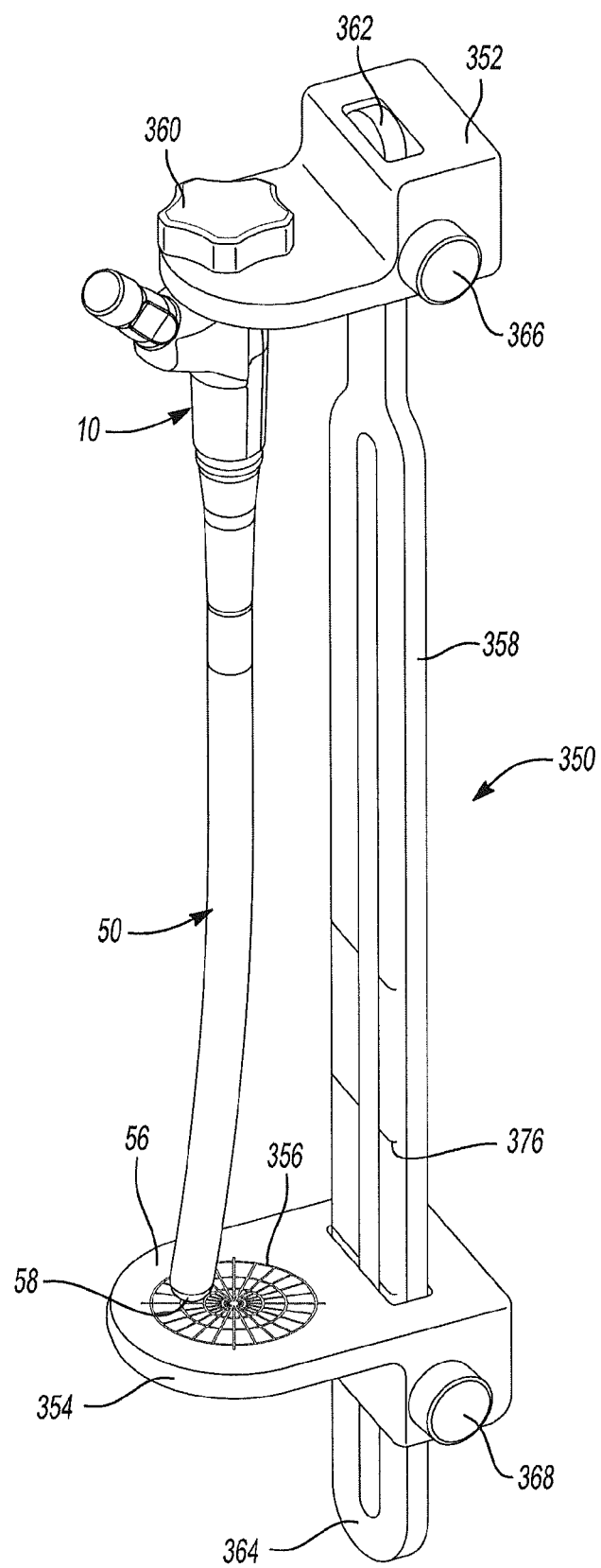
FIG. 24 is a perspective view of an additional alignment jig assembly according to the present teachings.
Figure 25:
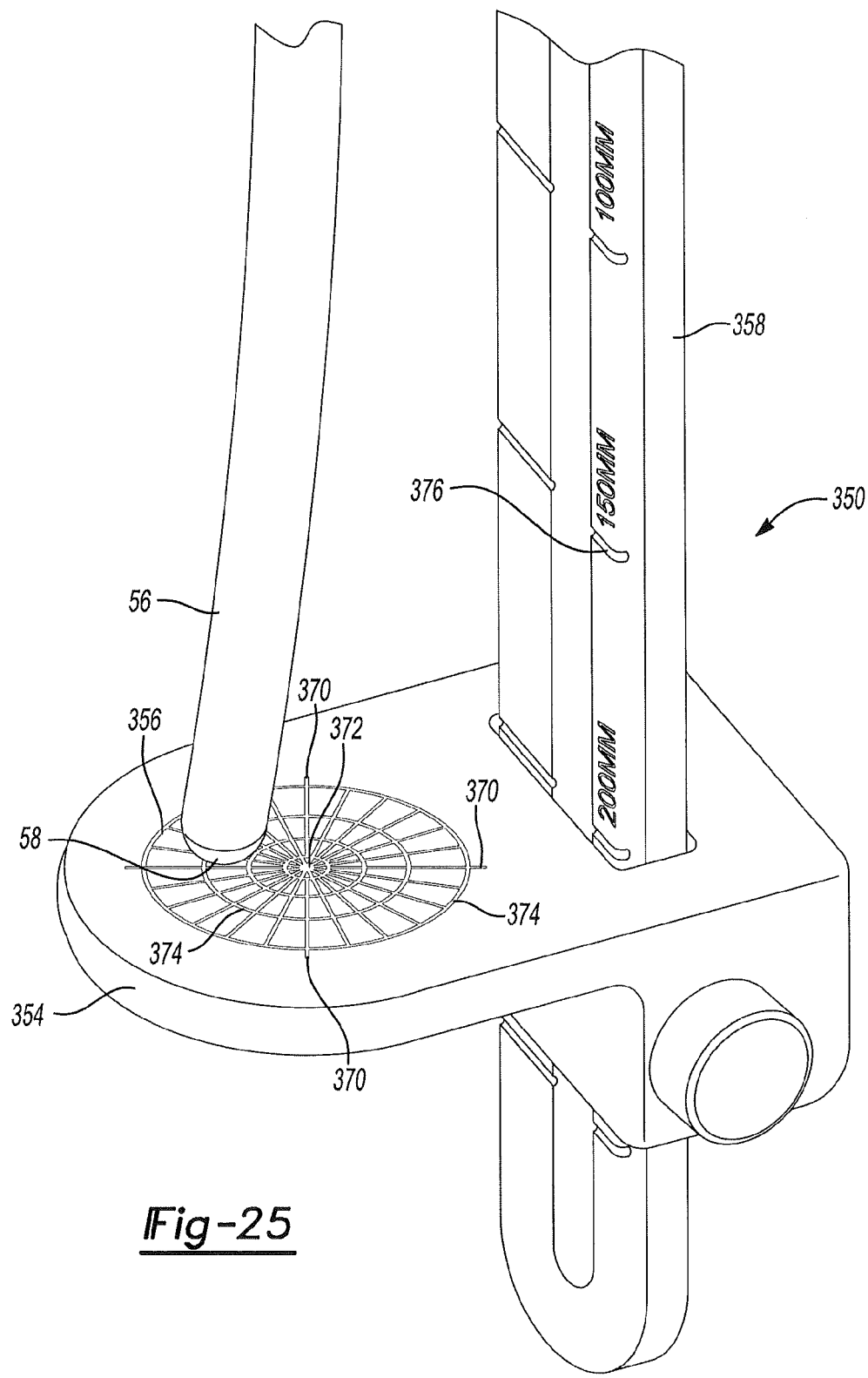
FIG. 25 is a close-up perspective view of a distal platform of the alignment jig assembly of FIG. 24.

With further reference to FIGS. 24 and 25, another alignment jig assembly according to the present teachings is illustrated at reference numeral 350. The alignment jig assembly 350 generally includes a proximal support portion 352, a distal platform 354 having a measuring grid 356, and a support base 358. The proximal support portion 352 is mounted proximate to a first end 362 of the support base 358. The position of the proximal support portion 352 along the support base 358 can be varied by loosening the proximal knob 366 and sliding the proximal support portion 352 along the support base 358 either proximal to or distal to the first end 362, and then tightening the proximal knob 366 to secure the proximal support portion 352 into its new position. The distal platform 354 is slidably mounted proximate to a second end 364 of the support base 358 that is opposite to the first end 362. The position of the distal platform 354 along the support base 358 can be varied by loosening the distal knob 368 and sliding the distal platform 354 along the support base 358 either proximal to or distal to the second end 364, and tightening the distal knob 368 to secure the distal portion 354 into its new position.

The trial proximal body 10 and the proximal body implant 176 can be mounted to the proximal support portion 352 in any suitable manner, such as with a mounting knob 360, which is structurally substantially similar to and operates in a manner substantially similar to the locking knob 86 of the alignment jig assembly 76.

The alignment jig assembly 350 can be used to identify or measure the angular orientation of the trial distal stem 50 relative to the trial proximal body 10 and to recreate the same orientation between the distal stem implant 200 and the proximal body implant 176 in substantially the same manner as described above with respect to the alignment jig assembly 76. When using the alignment jig assembly 350 the position of the stems 50 and 200 is measured using the measuring grid 356 rather than using the alignment tab 106. Further, the support base 358 includes markings that designate a position for the distal platform 354 depending on the length of the stems 50 and 200 used.

For example and as illustrated in FIG. 25, the measuring grid 356 includes a plurality of uniformly spaced markings, such as radial lines 370 emanating from a center point 372 and concentric circles 374 surrounding the center point 372. The position of the tip 58 with respect to the grid 356 can be noted by identifying the intersection of a particular radial line 370 with a particular concentric circle 374 that is closest to the tip 58. Also noted are the positions of the proximal support portion 352 and the distal platform 354 on the support base 358, such as by using the notations 376 corresponding to lengths of the trial distal stem 50. After removing the trial proximal body 10 and the trial distal stem 50 from the alignment jig assembly 76 by loosening the mounting knob 360, the proximal body implant 176, with the distal stem implant 200 mounted thereto, can be mounted to the alignment jig assembly 350 through cooperation between the mounting knob 360 and the threaded portion 42 of the proximal body implant 176. The distal stem implant 200 can be rotated such that its tip 58' is at the same intersection of the radial line 370 and the concentric circle 374 that the tip 58 was at, thereby providing the distal stem implant 200 with the same orientation as the trial distal stem 50.

While the present teachings describe trial and implant components of a modular femoral implant and a corresponding alignment jig assembly, the present teachings can also be applied to any other suitable modular implant where a stem is aligned relative to a body, including shoulder implants and knee implants, such as a tibial tray implant having an offset stem.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A modular femoral hip implant trialing system comprising:
   a trial proximal body including a neck having a head engagement trunnion and a proximal surface, the trial proximal body defining a proximal bore, a tapered distal bore adapted to receive a trial distal stem, and a passageway connecting the proximal bore to the distal bore, the proximal bore is axially aligned with the distal bore along a first axis;
   a fastener having a head in the proximal bore and a stem in the distal bore;
   a spring-type Belleville washer between the head and a base of the proximal bore; and
   a fastener retention member in the proximal bore, the retention member and the washer are on opposite sides of the head, the retention member includes an aperture having a diameter smaller than a diameter of the head to retain the fastener within the proximal bore,
   wherein the proximal body further defines a slot extending through the proximal bore along a second axis that is transverse to the first axis, the fastener retention member is seated within the slot,
   wherein the stem of the fastener is threaded and the fastener is movable to a first position in which the fastener cooperates with a threaded receptacle of a distal stem to retain the distal stem in the tapered distal bore such that the distal stem is free to rotate within the tapered distal bore during trialing; and
   wherein the fastener is movable to a second position in which the fastener extends further within the threaded receptacle than in the first position to retain the distal stem within the tapered distal bore to form a taper lock between the proximal body and the tapered distal bore.

2. The system of claim 1, further comprising a locking wedge defining a center bore having an inner diameter that is greater than an outer diameter of the stem of the fastener, the stem extends through the center bore thereby defining a gap between the outer diameter of the stem and the inner diameter of the locking wedge; and
   wherein the locking wedge is operable to move both along the first axis and transverse to the first axis to contact an inner surface of the distal bore.

3. The system of claim 2, wherein the stem of the fastener is threaded and the fastener is movable to a first position in which the fastener cooperates with a threaded receptacle of a distal stem to retain the distal stem in the distal bore and permit rotational movement of the distal stem relative to the locking wedge and the distal bore; and wherein the fastener is movable to a second position in which the fastener extends further within the threaded receptacle than in the first position to draw the distal stem further into the distal bore and move the locking wedge laterally with respect to the first axis such that the locking wedge contacts a sidewall of the distal bore and an angled proximal portion of the distal stem contacts the locking wedge to rotationally lock the distal stem and the locking wedge relative to the distal bore.

4. The system of claim 1 further comprising the distal stem with a tapered proximal portion operable to form a taper lock with a tapered portion of the distal bore.

5. The system of claim 1, further comprising an alignment jig operable to align the distal stem relative to the proximal body.

6. The system of claim 5, wherein the alignment jig includes:
   a proximal alignment jig portion;
   a distal alignment jig portion; and
   a support portion that extends between the proximal alignment jig portion and the distal alignment jig portion along a third axis to mount the proximal alignment jig portion to the distal alignment jig portion;
   wherein the support portion restricts rotational movement of the proximal alignment jig portion relative to the distal alignment jig portion; and
   wherein the support portion permits movement of the proximal alignment jig portion relative to the distal alignment jig portion along the third axis.

7. The system of claim 6, wherein the proximal alignment jig portion includes a locking device operable to secure the proximal body thereto and an engagement shaft proximate to the locking device operable to cooperate with the proximal body and restrict rotation of the proximal body, the locking device is aligned with an alignment device of the distal alignment jig portion along a fourth axis; and wherein the proximal body defines a slot at a proximal surface that is operable to cooperate with the engagement shaft to rotationally lock the proximal body to the alignment jig.

8. The system of claim 7, wherein the alignment device includes a grid on a surface of the distal alignment jig portion facing the proximal alignment jig portion, the grid includes a plurality of radial lines emanating from a center point and a plurality of concentric circles surrounding the center point; and wherein the alignment device includes a plurality of notations along the support portion corresponding to lengths of different distal stems.

9. The system of claim 5, wherein the alignment jig includes a first portion extending from a proximal alignment jig portion and a second portion extending from a distal alignment jig portion, the first portion is telescopingly received by the second portion to permit movement of the proximal alignment jig portion relative to the distal alignment jig portion along a second axis; and wherein the alignment jig includes a locking tab to lock the first portion relative to the second portion.

10. The system of claim 1, further comprising the trial distal stem having a proximal portion that includes a tapered outer diameter and a receptacle extending within the proximal portion.

11. The system of claim 10, wherein the fastener cooperates with the receptacle in a first position to secure the trial distal stem within the distal bore and permit rotation of the proximal body relative to the trial distal stem by spacing the tapered outer diameter of the trial distal stem apart from the tapered portion of the distal bore; and wherein the fastener cooperates with the receptacle in a second position to mate the tapered outer diameter of the trial distal stem with the tapered portion of the distal bore to form a taper lock there between, the fastener extends further within the distal bore in the second position than the first position.

12. A modular femoral hip implant trialing system comprising:
   a proximal body including a neck having a head engagement trunnion and a proximal surface, the proximal body defining a proximal bore, a distal bore adapted to receive a distal stem, and a passageway connecting the proximal bore to the distal bore, the proximal bore is axially aligned with the distal bore along a first axis;
   a fastener having a head in the proximal bore and a stem in the distal bore;
   a rotational locking device mounted in the distal bore and surrounding the stem including an inner diameter that is larger than an outer diameter of the stem;
   a fastener retention member in the proximal bore between the passageway and the head that is operable to retain the fastener within the proximal bore;
   wherein the proximal body further defines a slot extending through the proximal bore along a second axis that is transverse to the first axis, the fastener retention member is seated within the slot;
   wherein the fastener retention member is biased in a locked position in which a spring mounted within the slot biases an outer surface of the retention member in contact with a shoulder of the fastener to prevent the head from passing out of the proximal bore;
   wherein the stem of the fastener is threaded and the fastener is movable to a first position in which the fastener cooperates with a threaded receptacle of a distal stem having an angled proximal surface to retain the distal stem in the distal bore and permit rotational movement of the distal stem relative to the rotational locking device and the distal bore; and
   wherein the fastener is movable to a second position in which the fastener extends further within the threaded receptacle than in the first position to draw the distal stem further into the distal bore and move the rotational locking device laterally with respect to the first axis such that the rotational locking device contacts a sidewall of the distal bore and the angled proximal surface contacts an angled surface of the rotational locking device to rotationally lock the distal stem and the rotational locking device relative to the distal bore.

13. The system of claim 12, wherein the fastener retention member includes an aperture with a diameter larger than a diameter of the head to permit passage of the head there through.

14. The system of claim 12, further comprising an alignment jig operable to align a distal stem relative to the proximal body.

15. A modular femoral hip implant trialing method comprising:
   mounting a trial distal stem to a proximal trialing device by mating a first tapered surface of the trial distal stem with a second tapered surface of the proximal trialing device and by mating a fastening device of the proximal trialing device with a receptacle of the trial distal stem so as to permit rotation of the proximal trialing device with respect to the trial distal stem, where the proximal trialing device includes a proximal body having a neck with a head engagement trunnion in a proximal surface, the proximal body defining a proximal bore, a tapered distal bore having the second tapered surface adapted to receive the trial distal stem, and a passageway connecting the proximal bore to the distal bore, the proximal bore being axially aligned with the distal bore along a first axis;

positioning a spring-type Belleville washer between a head of the fastening device and a base of the proximal bore;

inserting a fastener retention member in a slot extending through the proximal bore along a second axis that is transverse to the first axis where the retention member and the washer are on opposite sides of the head and the retention member includes an aperture having a diameter smaller than a diameter of the head to retain the fastener within the proximal bore;

inserting the trial distal stem in an intramedullary canal of a femur for trialing to determine the appropriate orientation of the proximal trialing device relative to the trial distal stem;

locking the proximal trialing device to the trial distal stem by rotating the fastening device to drive the fastening device within the receptacle and to further mate the first tapered surface with the second tapered surface to prevent rotation therebetween after trialing;

mounting the proximal trialing device to a proximal portion of an alignment jig;

identifying and recording a position of the trial distal stem relative to the proximal trialing device with an alignment guide at a distal portion of the alignment jig;

removing the proximal trialing device with the trial distal stem mounted thereto from engagement with the alignment jig;

mounting a proximal body implant to the proximal portion of the alignment jig;

mounting a distal stem implant to the proximal body implant such that a tip of the distal stem implant approximates the position of the trial distal stem recorded relative to the alignment guide to provide the distal stem implant and the proximal body implant with a relative orientation that is similar to the orientation of the proximal trialing device relative to the distal stem implant during trialing; and implanting the distal stem implant with the proximal body implant mounted thereto in the intramedullary canal of the femur.

16. The method of claim 15, further comprising identifying the position of the trial distal stem relative to the proximal trialing device by setting an alignment tab of the alignment guide that is rotationally mounted to a distal portion of the alignment jig to approximate a position of the trial distal stem.

17. The method of claim 15, further comprising identifying the position of the trial distal stem relative to the proximal trialing device by recording a position of the trial distal stem with an alignment grid of the alignment guide having a plurality of intersecting lines emanating from a center point and concentric circles.

18. The method of claim 15, further comprising using the proximal trialing device to broach the implant site.

\* \* \* \* \*